(12) United States Patent
Zimmermann et al.

(10) Patent No.: US 7,919,489 B2
(45) Date of Patent: Apr. 5, 2011

(54) HETEROCYCLYAMIDE-SUBSTITUTED IMIDAZOLES

(75) Inventors: Holger Zimmermann, Wuppertal (DE); David Brueckner, Essen (DE); Kerstin Henninger, Wuppertal (DE); Ulrich Rosentreter, Binnen (DE); Martin Hendrix, Odenthal (DE); Joerg Keldenich, Wuppertal (DE); Dieter Lang, Velbert (DE); Martin Radtke, Erkrath (DE); Daniela Paulsen, Wuppertal (DE); Armin Kern, Wuppertal (DE)

(73) Assignee: Aicuris GmbH & Co. KG, Wuppertal (DE)

( * ) Notice: Subject to any disclaimer, the term of this patent is extended or adjusted under 35 U.S.C. 154(b) by 723 days.

(21) Appl. No.: 11/894,307

(22) Filed: Aug. 20, 2007

(65) Prior Publication Data

US 2008/0176859 A1    Jul. 24, 2008

Related U.S. Application Data

(63) Continuation of application No. PCT/EP2006/001325, filed on Feb. 14, 2006.

(30) Foreign Application Priority Data

Feb. 23, 2005  (DE) .................. 10 2005 008 183

(51) Int. Cl.
| | |
|---|---|
| *A61P 31/12* | (2006.01) |
| *A61K 31/4178* | (2006.01) |
| *A61K 31/4164* | (2006.01) |
| *C07D 401/12* | (2006.01) |
| *C07D 233/90* | (2006.01) |

(52) U.S. Cl. ............ 514/218; 514/252.11; 514/252.19; 514/253.09; 514/254.02; 514/254.05; 514/254.07; 540/575; 544/295; 544/357; 544/364; 544/369; 544/370

(58) Field of Classification Search ............ 514/218, 514/252.11, 252.19, 253.09, 254.02, 254.05, 514/254.07; 540/575; 544/295, 357, 364, 544/369, 370

See application file for complete search history.

(56) References Cited

U.S. PATENT DOCUMENTS

2008/0004275 A1   1/2008  Zimmermann et al.

FOREIGN PATENT DOCUMENTS

| | | |
|---|---|---|
| CA | 2 508 788 | 6/2004 |
| WO | WO-98/52558 | 11/1998 |
| WO | WO-99/23091 | 5/1999 |
| WO | WO-00/34261 | 6/2000 |
| WO | WO-00/42043 | 7/2000 |
| WO | WO-2004/052852 | 6/2004 |
| WO | WO-2005/092865 | 10/2005 |
| WO | WO-2006/089664 | 8/2006 |

OTHER PUBLICATIONS

Kuhle, Reactive Monomeric Carbonic Acid Derivatives, Angew. Chem. Internat. Edit., vol. 12, No. 8, pp. 630-643, 1973.*
Chong et al., Abstracts of 39th Interscience Conference on Antimicrobial Agents and Chemotherapy, 1999, p. 441.
Cinatl Jr. et al., FEMS Microbiology Reviews (2004) 28:59-77.
Kraemer et al., Cancer Research (1983) 43:4822-4827.
PCT Patent No. WO 2005/092865, International Publication Date: Oct. 6, 2005 (English abstract only).
English translation of the International Preliminary Report on Patentability for PCT/EP2006/001325, mailed Sep. 20, 2007, 9 pages.
Morissette et al., Advanced Drug Delivery Reviews (2004)56:275-300.
Vippagunta et al., Advanced Drug Delivery Reviews (2001)48:3-26.
"HIV-AIDS" Retrieved online via Internet [Mar. 25, 2009], URL: http://www.mayoclinic.com/health/hiv-aids/DS00005, Aug. 9, 2008.
Non-Final Office Action from U.S. Appl. No. 10/594,343, mailed on Mar. 30, 2009.
Amendment in Response to Non-Final Office Action from U.S. Appl. No. 10/594,343, filed Jun. 29, 2009.
Chaimbault et al., Pharmacy and Pharmacology Communications (1999) 5(3):211-215.

* cited by examiner

*Primary Examiner* — Brenda L Coleman

(74) *Attorney, Agent, or Firm* — Morrison & Foerster LLP

(57) ABSTRACT

The invention relates to heterocyclylamide-substituted imidazoles and methods for their preparation, their use for the treatment and/or prophylaxis of diseases as well as their use for the production of medicaments for the treatment and/or prophylaxis of diseases, in particular for the use as antiviral agents, especially against cytomegaloviruses.

9 Claims, No Drawings

HETEROCYCLYAMIDE-SUBSTITUTED IMIDAZOLES

CROSS-REFERENCE TO RELATED APPLICATIONS

This application is a continuation of pending international application PCT/EP 2006/001325, filed Feb. 14, 2006, designating US, which claims priority from German patent application DE 10 2005 008 183.5, filed Feb. 23, 2005. The contents of the above-referenced applications are incorporated herein by this reference in their entirety.

BACKGROUND OF THE INVENTION

The invention relates to heterocyclylamide-substituted imidazoles and methods for their preparation, their use for the treatment and/or prophylaxis of diseases as well as their use for the production of medicaments for the treatment and/or prophylaxis of diseases, in particular for use as antiviral agents, especially against cytomegaloviruses.

WO 99/23091 describes aromatic heterocyclic compounds as anti-inflammatory agents which, inter alia, may also be suitable for the treatment of viral infections.

Structurally different agents having antiviral activity are available on the market; however, the therapies currently available with ganciclovir, valganciclovir, foscarnet and cidofovir are associated with severe side effects, for example nephrotoxicity, neutropenia or thrombocytopenia. In addition, it is always possible for resistance to develop. Novel agents for an effective therapy are therefore desirable.

SUMMARY OF THE INVENTION

One object of the present invention is therefore to provide novel compounds having the same or improved antiviral activity for the treatment of viral infectious diseases in humans and animals.

It has been surprisingly found that the substituted imidazoles described in the present invention have high antiviral activity.

The present invention relates to compounds of formula

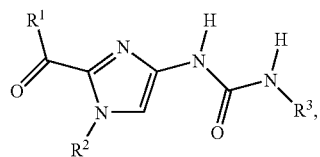

(I)

in which
$R^1$ represents a group of formula

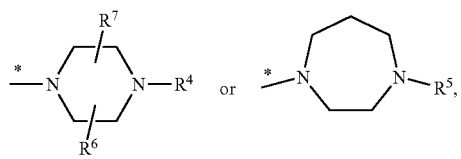

whereby
* represents the linkage site to the carbonyl group,
$R^4$ represents phenyl or 5- or 6-membered heteroaryl,
wherein phenyl and heteroaryl may be substituted with 1 to 3 substituents, whereby the substituents are selected independently of one another from the group consisting of halogen, hydroxy, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, $R^5$ represents phenyl or 5- or 6-membered heteroaryl,
wherein phenyl and heteroaryl may be substituted with 1 to 3 substituents, whereby the substituents are selected independently of one another from the group consisting of halogen, hydroxy, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, and
$R^6$ and $R^7$ independently of one another represent hydrogen, methyl or ethyl,
$R^2$ represents $C_1$-$C_6$-alkyl,
whereby alkyl may be substituted with a substituent, whereby the substituent is selected from the group consisting of $C_3$-$C_6$-cycloalkyl, $C_6$-$C_{10}$-aryl and 5- or 6-membered heteroaryl,
wherein cycloalkyl, aryl and heteroaryl may be substituted with 1 to 3 substituents, whereby the substituents are selected independently of one another from the group consisting of halogen, hydroxy, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
$R^3$ represents phenyl,
whereby phenyl may be substituted with 1 to 3 substituents, whereby the substituents are selected independently of one another from the group consisting of halogen, hydroxy, trifluoromethyl, difluoromethyl, trifluoromethoxy, difluoromethoxy, monofluoromethoxy, trifluoromethylthio, $C_1$-$C_6$-alkyl and $C_1$-$C_6$-alkoxy,
and their salts, their solvates and the solvates of their salts.

Compounds of the invention are the compounds of formula (I) and their salts, solvates and solvates of the salts; the compounds encompassed by formula (I) of the formulae mentioned below and their salts, solvates and solvates of their salts as well as the compounds encompassed by formula (I) and mentioned below as exemplary embodiments and their salts, solvates and solvates of their salts, insofar as the compounds mentioned below and encompassed by formula (I), are not already salts, solvates and solvates of the salts.

The compounds of the invention may, depending on their structure, exist in stereoisomeric forms (enantiomers, diastereomers). The invention therefore relates to the enantiomers or diastereomers and their respective mixtures. The stereoisomerically pure constituents can be isolated in a known manner from such mixtures of enantiomers and/or diastereomers.

Where the compounds of the invention can exist in tautomeric forms, the present invention includes all tautomeric forms.

Salts preferred for the purpose of the present invention are physiologically acceptable salts of the compounds of the invention. Also included, however, are salts which themselves are not suitable for pharmaceutical applications but which can be used, for example, for the isolation or purification of the compounds of the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases, such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purpose of the present invention refer to those forms of the compounds of the invention which in the solid or liquid state form a complex by coordination with solvent molecules. Hydrates are a special form of solvates in which the coordination takes place with water.

The present invention further also extends to prodrugs of the compounds of the invention. The term "prodrugs" encompasses compounds which themselves may be biologically active or inactive but which, during their residence time in the body, are converted into compounds of the invention (for example metabolically or hydrolytically).

For the purpose of the present invention, the substituents have the following meaning, unless specified otherwise:

Alkyl per se and "alk" and "alkyl" in alkoxy, alkylamino, alkoxycarbonyl and alkylaminocarbonyl represent a straight-chain or branched alkyl radical generally having 1 to 6 ("$C_1$-$C_6$-alkyl"), preferably 1 to 4, particularly preferably 1 to 3, carbon atoms, by way of example and preferably methyl, ethyl, n-propyl, isopropyl, tert-butyl, n-pentyl and n-hexyl.

Alkoxy, by way of example and preferably, represents methoxy, ethoxy, n-propoxy, isopropoxy, tert-butoxy, n-pentoxy and n-hexoxy.

Alkylamino represents an alkylamino radical having one or two alkyl substituents (selected independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino. $C_1$-$C_3$-Alkylamino represents, for example, a monoalkylamino radical having 1 to 3 carbon atoms or a dialkylamino radical having 1 to 3 carbon atoms per alkyl substituent.

Alkoxycarbonyl, by way of example and preferably, represents methoxycarbonyl, ethoxycarbonyl, n-propoxycarbonyl, isopropoxycarbonyl, tert-butoxycarbonyl, n-pentoxycarbonyl and n-hexoxycarbonyl.

Alkylaminocarbonyl represents an alkylaminocarbonyl radical having one or two alkyl substituents (selected independently of one another), by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentylaminocarbonyl and N-n-hexyl-N-methylaminocarbonyl. $C_1$-$C_3$-Alkylaminocarbonyl represents, for example, a monoalkylaminocarbonyl radical having 1 to 3 carbon atoms or a dialkylaminocarbonyl radical having 1 to 3 carbon atoms per alkyl substituent.

Aryl represents a mono- or bicyclic aromatic carbocyclic radical usually having 6 to 10 carbon atoms; by way of example and preferably phenyl and naphthyl.

For the purpose of the invention, 5- or 6-membered heteroaryl generally represents an aromatic monocyclic radical having 5 or 6 ring atoms and up to 4 heteroatoms from the group consisting of S, O and/or N. The heteroaryl radical may be attached via a carbon atom or a heteroatom. The following radicals may be mentioned by way of example and preferably: thienyl, furyl, pyrrolyl, thiazolyl, oxazolyl, pyrazolyl, imidazolyl, pyridyl, pyrimidyl and pyridazinyl.

Cycloalkyl represents a cycloalkyl group usually having 3 to 8, preferably 3 to 6, carbon atoms, by way of example and preferably cyclopropyl, cyclobutyl, cyclopentyl, cyclohexyl and cycloheptyl.

Halogen represents fluorine, chlorine, bromine and iodine.

For the purpose of the present invention, preference is given to compounds of formula (I),
in which
$R^1$ represents a group of formula

whereby
* represents the linkage site to the carbonyl group,
$R^4$ represents phenyl or 5- or 6-membered heteroaryl,
wherein phenyl and heteroaryl may be substituted with 1 to 3 substituents, whereby the substituents are selected independently of one another from the group consisting of halogen, hydroxy, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, $R^2$ represents $C_1$-$C_6$-alkyl,
whereby alkyl may be substituted with a substituent, whereby the substituent is selected from the group consisting of $C_3$-$C_6$-cycloalkyl and phenyl,
wherein cycloalkyl and phenyl may be substituted with 1 to 3 substituents, whereby the substituents are selected independently of one another from the group consisting of halogen, hydroxy, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, $R^3$ represents phenyl,
whereby phenyl may be substituted with 1 to 3 substituents, whereby the substituents are selected independently of one another from the group consisting of halogen, hydroxy, trifluoromethyl, difluoromethyl, trifluoromethoxy, difluoromethoxy, monofluoromethoxy, trifluoromethylthio, $C_1$-$C_6$-alkyl and $C_1$-$C_6$-alkoxy, and their salts, their solvates and the solvates of their salts.

For the purpose of the present invention, preference is also given to compounds of formula (I),
in which
R¹ represents a group of formula

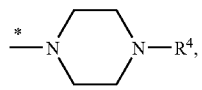

whereby
* represents the linkage site to the carbonyl group,
R⁴ represents phenyl or pyridyl,
wherein phenyl and pyridyl may be substituted with 1 to 3 substituents, whereby the substituents are selected independently of one another from the group consisting of halogen, nitro, cyano, trifluoromethyl, difluoromethyl, trifluoromethoxy, difluoromethoxy, monofluoromethoxy, $C_1$-$C_4$-alkyl and $C_1$-$C_4$-alkoxy,
R² represents methyl, ethyl or n-butyl,
whereby methyl, ethyl and n-butyl may be substituted with a substituent, whereby the substituent is selected from the group consisting of cyclopropyl and phenyl,
wherein phenyl may be substituted with a trifluoromethyl substituent,
R³ represents phenyl,
whereby phenyl may be substituted with 1 to 3 substituents, whereby the substituents are selected independently of one another from the group consisting of fluorine, chlorine, trifluoromethoxy, difluoromethoxy, trifluoromethylthio and methyl,
and their salts, their solvates and the solvates of their salts.

For the purpose of the present invention, preference is also given to compounds of formula (I) in which R¹ represents a group of formula

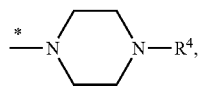

whereby
* represents the linkage site to the carbonyl group, and
R⁴ represents phenyl or pyridyl,
wherein phenyl and pyridyl may be substituted with 1 to 3 substituents, whereby the substituents are selected independently of one another from the group consisting of halogen, nitro, cyano, trifluoromethyl, difluoromethyl, trifluoromethoxy, difluoromethoxy, monofluoromethoxy, $C_1$-$C_4$-alkyl and $C_1$-$C_4$-alkoxy.

For the purpose of the present invention, preference is also given to compounds of formula (I) in which R³ represents phenyl, whereby phenyl may be substituted with 1 to 3 substituents, whereby the substituents are selected independently of one another from the group consisting of fluorine, chlorine, trifluoromethoxy, difluoromethoxy, trifluoromethylthio and methyl.

The invention furthermore relates to a method for the preparation of the compounds of formula (I) whereby
according to method [A] compounds of formula

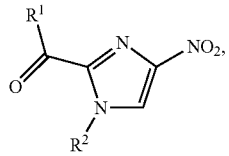

in which
R¹ and R² have the meaning indicated above,
are reacted in the first step with a reducing agent and in the second step in the presence of a carbonic acid derivative with compounds of formula $$H_2N—R^3 \quad (III),$$

in which
R³ has the meaning indicated above,
or
according to method [B] compounds of formula (II) are reacted in the first step with a reducing agent and in the second step with compounds of formula $$OCN—R^3 \quad (IV),$$

in which
R³ has the meaning indicated above,
or
according to method [C] compounds of formula

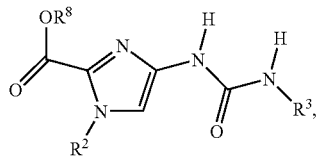

in which
R² and R³ have the meaning indicated above, and
R⁸ represents methyl or ethyl,
are reacted in the first step with a base and in the second step with compounds of formula $$R^1—H \quad (VI),$$

in which
R¹ has the meaning indicated above,
in the presence of dehydrating reagents.

The compounds of formulae (III), (IV) and (VI) are known or can be synthesized by known methods from the corresponding starting materials.

For methods [A] and [B], step 1, the following applies:

The reaction generally takes place in inert solvents, preferably in a temperature range from 0° C. to the reflux of the solvents under atmospheric pressure to 3 bar.

Reducing agents are, for example, palladium-on-carbon and hydrogen, formic acid/triethylamine/palladium-on-carbon, zinc, zinc/hydrochloric acid, iron, iron/hydrochloric acid, iron(II) sulfate/hydrochloric acid, sodium sulfide, sodium disulfide, sodium dithionite, ammonium polysulfide, sodium borohydride/nickel chloride, tin dichloride, titanium trichloride or Raney nickel and an aqueous hydrazine solution; preference is given to Raney nickel and an aqueous hydrazine solution, palladium-on-carbon and hydrogen or formic acid/triethylamine/palladium-on-carbon.

Inert solvents are, for example, ethers, such as diethyl ether, methyl tert-butyl ether, 1,2-dimethoxyethane, dioxane, tetrahydrofuran, glycol dimethyl ether or diethylene glycol dimethyl ether, alcohols, such as methanol, ethanol, n-propanol, isopropanol, n-butanol or tert-butanol, hydrocarbons, such as benzene, xylene, toluene, hexane, cyclohexane or mineral oil fractions, or other solvents, such as dimethylformamide, dimethylacetamide, acetonitrile or pyridine, in the case of water-miscible solvents also mixtures of the same with water; preferred solvents are methanol, ethanol, isopropanol or, in the case of Raney nickel and an aqueous hydrazine solution, tetrahydrofuran.

For method [A], step 2, the following applies:

The reaction generally takes place in inert solvents, preferably in a temperature range of from room temperature to 40° C. under atmospheric pressure.

Carbonic acid derivatives are, for example, N,N-carbonyldiimidazole, phosgene, diphosgene, triphosgene, phenyl chloroformate or 4-nitrophenyl chloroformate; preference is given to N,N-carbonyldiimidazole.

Inert solvents are, for example, halohydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as ethyl acetate, acetone, dimethylformamide, dimethylacetamide, 2-butanone, dimethyl sulfoxide, acetonitrile or pyridine, in the case of water-miscible solvents also mixtures of the same with water; preference is given to dimethyl sulfoxide.

For method [B], step 2, the following applies:

The reaction generally takes place in inert solvents, optionally in the presence of a base, preferably in a temperature range of from room temperature to the reflux of the solvents under atmospheric pressure.

Inert solvents are, for example, halohydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as ethyl acetate, acetone, dimethylformamide, dimethylacetamide, 2-butanone, dimethyl sulfoxide, acetonitrile or pyridine; preference is given to tetrahydrofuran or methylene chloride.

Bases are, for example, alkali metal carbonates, such as cesium carbonate, sodium carbonate or potassium carbonate, or potassium tert-butoxide, or other bases, such as sodium hydride, DBU, triethylamine or diisopropylethylamine, preferably triethylamine.

For method [C], step 1, the following applies:

The reaction generally takes place in inert solvents, preferably in a temperature range of from 0° C. to the reflux of the solvents under atmospheric pressure.

Bases are, for example, alkali metal hydroxides, such as sodium hydroxide, lithium hydroxide or potassium hydroxide, or alkali metal carbonates, such as cesium carbonate, sodium carbonate or potassium carbonate, preferably sodium hydroxide.

Inert solvents are, for example, halohydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, alcohols, such as methanol, ethanol, n-propanol, isopropanol, n-butanol or tert-butanol, hydrocarbons, such as benzene, xylene, toluene, hexane, cyclohexane or mineral oil fractions, or other solvents, such as dimethylformamide, dimethylacetamide, dimethyl sulfoxide, acetonitrile or pyridine, or mixtures of solvents with water; the preferred solvent is a mixture of ethanol and water.

For method [C], step 2, the following applies:

The reaction generally takes place in inert solvents, optionally in the presence of a base, preferably in a temperature range of from −70° C. to 40° C. under atmospheric pressure.

Suitable dehydrating reagents hereby include, for example, carbodiimides, such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds, such as carbonyldiimidazole, or 1,2-oxazolium compounds, such as 2-ethyl-5-phenyl-1,2-oxazolium-3-sulfate or 2-tert-butyl-5-methylisoxazolium perchlorate, or acylamino compounds, such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or mixtures of these, with bases.

Bases are, for example, alkali metal carbonates, such as, for example, sodium carbonate or potassium carbonate, or sodium bicarbonate or potassium bicarbonate, or organic bases, such as trialkylamines, for example triethylamine, N-methylmorpholine, N-methylpiperidine, 4-dimethylaminopyridine or diisopropylethylamine, or DBU, DBN, pyridine; preference is given to triethylamine.

The condensation is preferably carried out using carbonyldiimidazole.

Inert solvents are, for example, halohydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as ethyl acetate, acetone, dimethylformamide, dimethylacetamide, 2-butanone, dimethyl sulfoxide, acetonitrile or pyridine, in the case of water-miscible solvents also mixtures of the same with water; preference is given to dimethylformamide.

The compounds of formula (II) are known or can be prepared by reacting compounds of formula

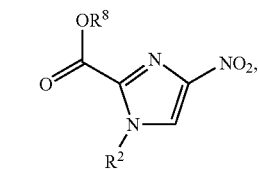
(VII)

in which $R^2$ has the meaning indicated above, and $R^8$ represents methyl or ethyl, in the first step with a base and in the second step with compounds of formula (VI), in the presence of dehydrating reagents.

The reaction takes place as described in method [C].

The compounds of formula (VII) are known or can be prepared by reacting compounds of formula

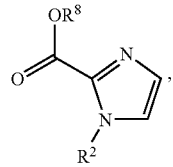
(VIII)

in which $R^2$ has the meaning indicated above, and $R^8$ represents methyl or ethyl, with fuming nitric acid, concentrated nitric acid, nitrating acid or other mixing ratios of sulfuric acid and nitric acid, optionally in acetic anhydride as solvent, preferably in a temperature range of from room temperature to 60° C. under atmospheric pressure.

The compounds of formula (V) are known or can be prepared by reacting compounds of formula (VII) in the first step with a reducing agent and in the second step in the presence of a carbonic acid derivative with compounds of formula (III) or in the second step with compounds of formula (IV).

The reaction takes place as described in methods [A] and [B].

The compounds of formulae (III), (IV), (VI) and (VIII) are known or can be prepared by known methods from the corresponding starting materials.

Synthesis scheme 1:

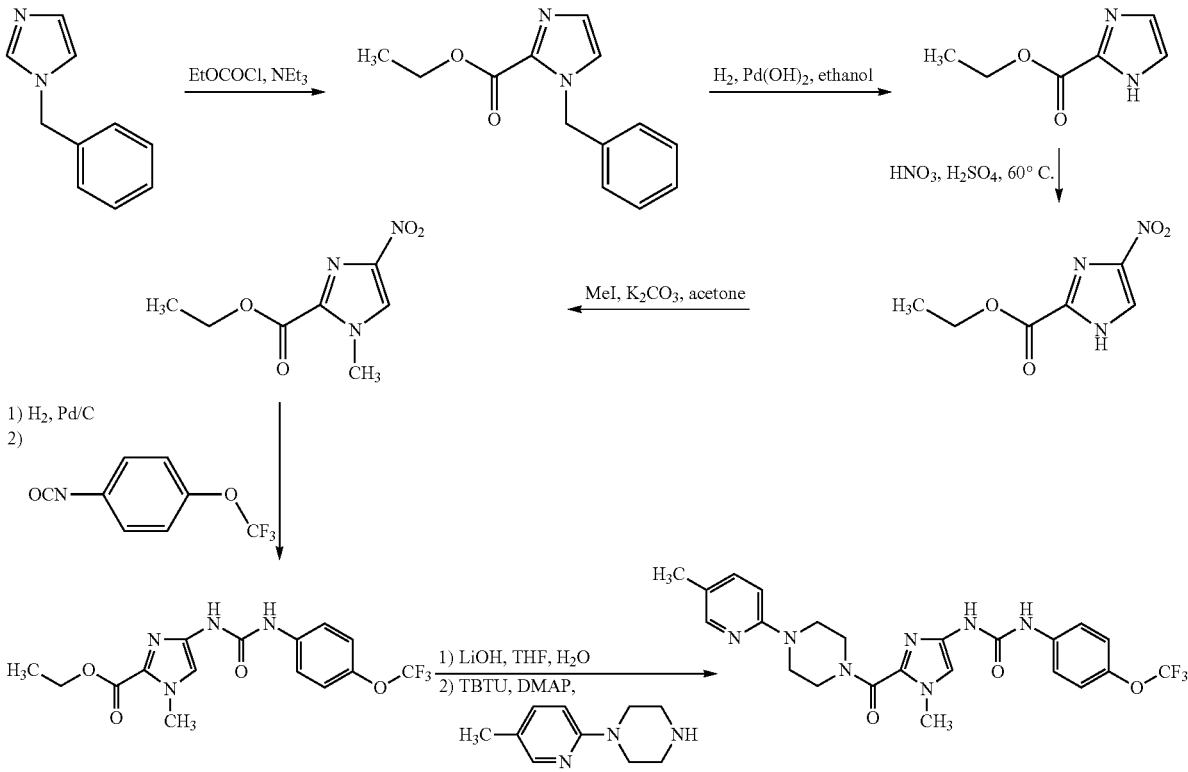

Synthesis scheme 2:

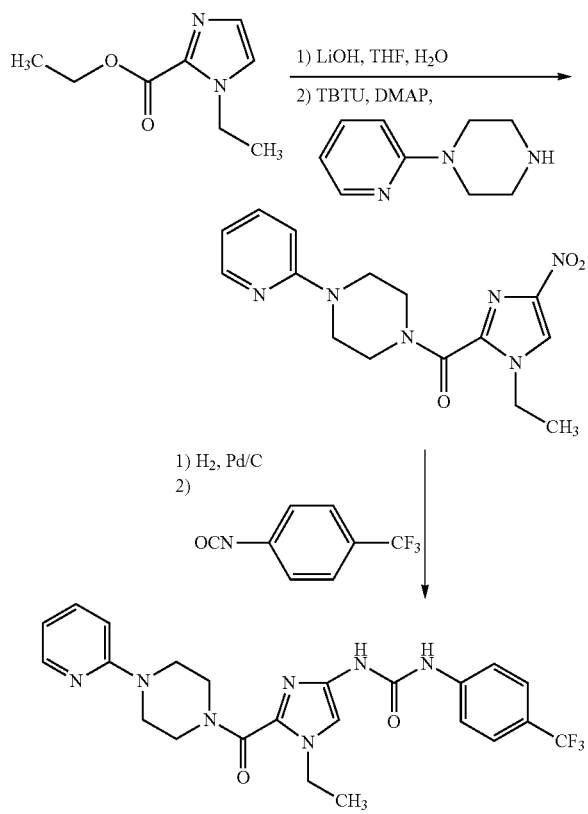

The compounds of general formula (I) of the invention show an unforeseeable, surprising spectrum of activity. They have antiviral activity on representatives of the group of *Herpes viridae* (herpes viruses), especially on cytomegaloviruses (CMV), in particular on the human cytomegalovirus (HCMV). They are thus suitable for the treatment and prophylaxis of diseases, especially infections with viruses, in particular the viruses mentioned above, and the infectious diseases caused thereby. Hereinafter, a viral infection is to be understood as meaning both an infection with a virus and a disease caused by an infection with a virus.

Due to their particular properties, the compounds of general formula (I) can be used for the production of medicaments suitable for the prophylaxis and/or treatment of diseases, in particular viral infections.

Areas of indication which may be mentioned by way of example are:

1) Treatment and prophylaxis of HCMV infections in AIDS patients (retinitis, pneumonitis, gastrointestinal infections).

2) Treatment and prophylaxis of cytomegalovirus infections in bone-marrow and organ transplant patients who develop often life-threatening HCMV pneumonitis or encephalitis, and gastrointestinal and systemic HCMV infections.

3) Treatment and prophylaxis of HCMV infections in neonates and infants.

4) Treatment of an acute HCMV infection in pregnant women.

5) Treatment of an HCMV infection in immunosuppressed patients associated with cancer and cancer therapy.

6) Treatment of HCMV-positive cancer patients with the aim of reducing HCMV-mediated tumor progression (cf. J. Cinatl, et al., *FEMS Microbiology Reviews* 2004, 28, 59-77).

The compounds of the invention are preferably used for the production of medicaments suitable for the prophylaxis and/or treatment of infections with a representative of the group of *Herpes viridae*, in particular a cytomegalovirus, especially the human cytomegalovirus.

Due to their pharmacological properties, the compounds of the invention can be used alone and, if required, also in combination with other active compounds, in particular antiviral active compounds, such as, for example, gancyclovir or acyclovir, for the treatment and/or prevention of viral infections, in particular HCMV infections.

The present invention furthermore relates to the use of the compounds of the invention for the treatment and/or prophylaxis of diseases, preferably of viral infections, in particular of infections with the human cytomegalovirus (HCMV) or another representative of the group of *Herpes viridae*.

The present invention furthermore relates to the use of the compounds of the invention for the treatment and/or prophylaxis of diseases, in particular the diseases mentioned above.

The present invention furthermore relates to the use of the compounds of the invention for the production of a medicament for the treatment and/or prophylaxis of diseases, in particular the diseases mentioned above.

The present invention furthermore relates to a method for the treatment and/or prophylaxis of diseases, in particular the diseases mentioned above, using an antivirally effective amount of the compounds of the invention.

The compounds of the invention can act systemically and/or locally. For this purpose, they can be administered in a suitable way, such as, for example, orally, parenterally, pulmonarily, nasally, sublingually, lingually, buccally, rectally, dermally, transdermally, conjunctivally or otically, or as an implant or stent.

For these administration routes, it is possible to administer the compounds of the invention in suitable administration forms.

Suitable for oral administration are administration forms which function according to the prior art and release the compounds of the invention rapidly and/or in modified form, and which comprise the compounds of the invention in crystalline and/or amorphicized and/or dissolved form, such as, for example, tablets (uncoated and coated tablets, for example having enteric coatings or coatings which dissolve with a delay or which are insoluble and which control the release of the compound of the invention), tablets or films/wafers, which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of an absorption (for example intramuscularly, subcutaneously, intracutaneously, percutaneously or intraperitonealy). Administration forms suitable for parenteral administration are, inter alia, preparations for injection and infusion in the form of solutions, suspensions, emulsions, lyophilisates or sterile powders.

Examples suitable for the other administration routes are pharmaceutical forms for inhalation (inter alia powder inhalers, nebulizers), nasal drops, solutions, sprays; tablets, films/wafers or capsules, to be administered lingually, sublingually or buccally, suppositories, preparations for ears or eyes, vaginal capsules, aqueous suspensions (lotions, shaking mixtures), lipophilic suspensions, ointments, creams, transdermal therapeutic systems, milk, pastes, foams, dusting powders, implants or stents.

The compounds of the invention can be converted into the stated administration forms. This can take place in a manner known per se by mixing with inert nontoxic, pharmaceutically acceptable excipients. These excipients include, inter alia, carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), colors (for example inorganic pigments, such as, for example, iron oxides) and taste- and/or odor-corrigents.

The present invention furthermore relates to medicaments comprising at least one compound of the invention, usually together with one or more inert nontoxic, pharmaceutically acceptable excipients, and their use for the purposes mentioned above.

In general, it has proved advantageous to administer on intravenous administration amounts of about 0.001 to 10 mg/kg, preferably about 0.01 to 5 mg/kg, of body weight to achieve effective results, and the dosage on oral administration is about 0.01 to 25 mg/kg, preferably 0.1 to 10 mg/kg, of body weight.

It may nevertheless be necessary, where appropriate, to deviate from the amounts mentioned, specifically depending on body weight, administration route, individual response to the active compound, type of preparation and time or interval over which the administration takes place. Thus, in some cases it may be sufficient to make do with less than the aforementioned minimum amount, whereas in other cases the upper limit mentioned must be exceeded. In the event of an administration of larger amounts, it may be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

DETAILED DESCRIPTION OF PREFERRED EMBODIMENTS

A. Examples

Abbreviations Used:
aqu. Aqueous
BINAP 2,2'-Bis(diphenylphosphino)-1,1'-binaphthyl
$CD_3CN$ Deuteroacetonitrile
conc. Concentrated
DCI Direct chemical ionization (in MS)
DCM Dichloromethane
DIEA N,N-Diisopropylethylamine (Hünig's base)
dil. Dilute
DMAP 4-N,N-Dimethylaminopyridine
DMF N,N-Dimethylformamide
DMSO Dimethyl sulfoxide
EA Ethyl acetate
EDCIxHCl N'-(3-Dimethylaminopropyl)-N-ethylcarbodiimide hydrochloride
EI Electron impact ionization (in MS)
ESI Electrospray ionization (in MS)
Ex. Example
h Hour
HATU O-(7-Azabenzotriazol-1-yl)-N,N,N',N'-tetramethyluronium hexafluorophosphate
HBTU O-(Benzotriazol-1-yl)-N,N,N',N'-tetramethyluronium hexafluorophosphate
HPLC High pressure, high performance liquid chromatography
LC-MS Liquid chromatography-coupled mass spectroscopy
LDA Lithium diisopropylamide
lit. Literature (reference)
m.p. Melting point
MS Mass spectroscopy
NMR Nuclear magnetic resonance spectroscopy
RP-HPLC Reverse phase HPLC
RT Room temperature
$R_t$ Retention time (in HPLC)
sat. Saturated
sol. Solution
TBTU O-(Benzotriazol-1-yl)-N,N,N',N'-tetramethyluronium tetrafluoroborate
THF Tetrahydrofuran
TLC Thin-layer chromatography HPLC and LC-MS Methods:

Method 1 (LC-MS): Instrument: Micromass Platform LCZ with HPLC Agilent series 1100; column: Thermo HyPURITY Aquastar 3μ 50 mm×2.1 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 2 (LC-MS): Instrument: Micromass Quattro LCZ with HPLC Agilent series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 3 (LC-MS): Instrument: Micromass Platform LCZ with HPLC Agilent series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4 (LC-MS): MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 5 (LC-MS): MS instrument type: Micromass ZQ; HPLC instrument type: HP 1100 series; UV DAD; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 6 (LC-MS): MS instrument type: Micromass ZQ; HPLC instrument type: HP 1100 series; UV DAD; column: Grom-Sil 120 ODS-4 HE 50 mm×2 mm, 3.0 μm; eluent A: water+500 μl of 50% formic acid/l, eluent B: acetonitrile+500 μl of 50% formic acid/l; gradient: 0.0 min 0% B→2.9 min 70% B→3.1 min 90% B→4.5 min 90% B; oven: 50° C.; flow rate: 0.8 ml/min; UV detection: 210 nm.

Method 7 (LC-MS): MS instrument type: Micromass ZQ; HPLC instrument type: Waters Alliance 2795; column: Merck Chromolith SpeedROD RP-18e 50 mm×4.6 mm; eluent A: water+500 µl of 50% formic acid/l; eluent B: acetonitrile+500 µl of 50% formic acid/l; gradient: 0.0 min 10% B→3.0 min 95% B→4.0 min 95% B; oven: 35° C.; flow rate: 0.0 min 1.0 ml/min→3.0 min 3.0 ml/min→4.0 min 3.0 ml/min; UV detection: 210 nm.

Method 8 (LC-MS): Instrument: Micromass Quattro LCZ, with HPLC Agilent series 1100; column: Grom-SIL120 ODS-4 HE, 50 mm×2.0 mm, 3 µm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208400 nm.

Method 9 (GC-MS): Instrument: Micromass GCT, GC6890; column: Restek RTX-35MS, 30 m×250 µm×0.25 µm; constant helium flow rate: 0.88 ml/min; oven: 60° C.; inlet: 250° C.; gradient: 60° C. (maintained for 0.30 min), 50° C./min→120° C., 16° C./min→250° C., 30° C./min→300° C. (maintained for 1.7 min).

Method 10 (analytical HPLC): column: Kromasil 100 RP-18, 60 mm×2.1 mm, 3.5 µm; eluent A: water+0.5% perchloric acid (70%), eluent B: acetonitrile; gradient: 0 min 2% B, 0.5 min 2% B, 4.5 min 90% B, 9 min 90% B, 9.2 min 2% B, 10 min 2% B; flow rate: 0.75 ml/min; column temperature: 30° C.; detection: UV 210 nm.

Starting Compounds

Example 1A

Ethyl 1-benzyl-1H-imidazole-2-carboxylate

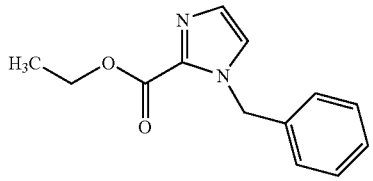

148 g (936 mmol) of 1-benzyl-1H-imidazole are suspended in 480 ml of acetonitrile and, at −20° C., 120 ml (87.1 g; 860 mmol) of triethylamine are added. Over a period of 15 minutes, 211.2 ml (239 g; 2208 mmol) of ethyl chloroformate are then added dropwise. The reaction mixture is stirred at −20° C. for 10 minutes. After warming to 15 to 20° C., the reaction mixture is stirred for 18 h and then concentrated in vacuo. Water, a saturated sodium chloride solution and a saturated sodium bicarbonate solution are added to the residue, and the mixture is extracted three times with ethyl acetate. The combined organic phases are washed with a saturated sodium chloride solution and, after drying with magnesium sulfate, concentrated in vacuo. The residue is subjected to a fractional distillation under high vacuum (boiling point=173 to 181° C., pressure=1.7 to 1.2 mbar).

Yield: 122.6 g (46% of theory)

LC-MS (Method 4): $R_t$=1.71 min.

MS (ESI$^+$): m/z=231 [M+H]$^+$ $^1$H-NMR (300 MHz, DMSO-d$_6$): δ=7.6 (s, 1H), 7.4-7.1 (m, 6H), 5.2 (s, 2H), 4.25 (q, 2H), 1.25 (tr, 3H) ppm.

Example 2A

Ethyl imidazole-2-carboxylate

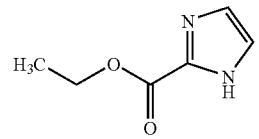

34.7 g (150.9 mmol) of ethyl 1-benzyl-1H-imidazole-2-carboxylate are dissolved in 1005 ml of ethanol, and 34 g of ammonium formate are added. The reaction mixture is heated under reflux for about 6 h. A total of 8 g of 10% palladium-on-carbon and 18 g of ammonium formate are thereby added in small portions. After cooling, the catalyst is filtered off and the filtrate is concentrated in vacuo. The product that crystallizes out during this operation is triturated with 80 ml of ice-water and collected by suction filtration.

Yield: 15.9 g (75% of theory)

MS (ESI$^+$): m/z=141 [M+H]$^+$ $^1$H-NMR (200 MHz, DMSO-d$_6$): δ=13.3 (s broad, 1H), 7.4 (s, 1H), 7.15 (s, 1H), 4.3 (q, 2H), 1.3 (tr, 3H) ppm.

Example 3A

Ethyl 4-nitro-1H-imidazole-2-carboxylate

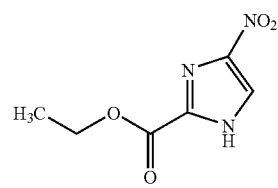

While cooling on ice, 16.08 g (114.7 mmol) of ethyl imidazole-2-carboxylate are dissolved in 71.7 ml of concentrated sulphuric acid. 71.7 ml of 100% fuming nitric acid are then added dropwise. The reaction solution is stirred at 50 to 60° C. for 3 h and, after cooling, poured onto 800 ml of an ice/water mixture. The precipitated crystals are collected by suction filtration and washed with 1500 ml of ice-water.

Yield: 15 g (70% of theory)

MS (ESI$^+$): m/z=186 [M+H]$^+$ $^1$H-NMR (300 MHz, DMSO-d$_6$): δ=14.5 (s broad, 1H), 8.5 (s, 1H), 4.4 (q, 2H), 1.35 (tr, 3H), ppm.

Example 4A 4-({[(4-Chloro-2-methylphenyl)amino]carbonyl}amino)-1-(cyclopropylmethyl)-1H-imidazole-2-carboxylic acid

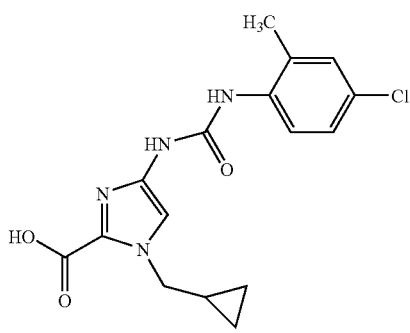

Step 1

Ethyl 1-(cyclopropylmethyl)-4-nitro-1H-imidazole-2-carboxylate

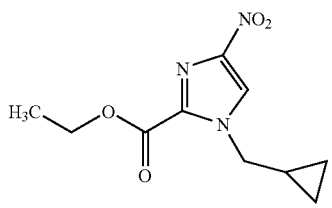

Under argon, 15 g (81 mmol) of ethyl 4-nitro-1H-imidazole-2-carboxylate are stirred with 13.13 g (97.2 mmol) of cyclopropylmethyl bromide and 22.4 g (162 mmol) of potassium carbonate in 165 ml of DMF at 80° C. for 1 h. After cooling, the reaction mixture is diluted with water and extracted four times with ethyl acetate. The combined organic phases are washed once with water and three times with a saturated sodium chloride solution, dried with magnesium sulfate and concentrated in vacuo. The crystalline residue is directly used further for the next reaction.

Yield: 17.59 g (70% of theory)
LC-MS (Method 2): $R_t$=2.02 min.
MS (ESI$^+$): m/z=240 [M+H]$^+$
$^1$H-NMR (300 MHz, DMSO-d$_6$): δ=8.2 (s, 1H), 4.4 (q, 2H), 4.3 (d, 2H), 1.4 (m, 4H), 0.55 (q, 2H), 0.45 (q, 2H) ppm.

Step 2

Ethyl 4-amino-1-(cyclopropylmethyl)-1H-imidazole-2-carboxylate

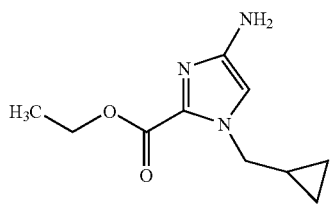

3.89 g (16.26 mmol) of ethyl 1-(cyclopropylmethyl)-4-nitro-1H-imidazole-2-carboxylate are dissolved in 50 ml of THF, and a spatula tip of Raney nickel is added. In a hydrogenation apparatus, the reaction mixture is hydrogenated with hydrogen at room temperature. The catalyst is filtered off and the filtrate is concentrated in vacuo. The concentration residue is directly used further for the next reaction.

Yield: 3.46 g (100% of theory)
LC-MS (Method 3): $R_t$=1.21 min.
MS (ESI$^+$): m/z=210 [M+H]$^+$
$^1$H-NMR (300 MHz, DMSO-d$_6$): δ=6.55 (s, 1H), 4.55 (s, 2H), 4.2 (q, 2H), 4.1 (d, 2H), 1.25 (tr, 3H), 1.2 (m, 1H), 0.5 (q, 2H), 0.3 (q, 2H) ppm.

Step 3

Ethyl 4-({[(4-chloro-2-methylphenyl)amino]carbonyl}amino)-1-(cyclopropylmethyl)-1H-imidazole-2-carboxylate

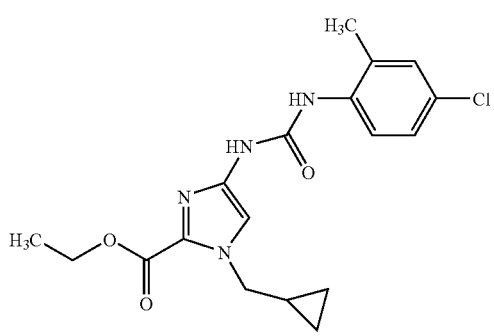

Under argon, 6 g (35.8 mmol) of 3-chloro-4-phenyl isocyanate are added to 7.49 g (35.8 mmol) of ethyl 4-amino-1-(cyclopropylmethyl)-1H-imidazole-2-carboxylate in 18 ml of THF, and the mixture is stirred at room temperature for 4 h. The reaction mixture is concentrated in vacuo and the product which crystallizes from the mixture is triturated with 40 ml of ethyl acetate and collected by suction filtration.

Yield: 11.1 g (82% of theory)
LC-MS (Method 2): $R_t$=2.66 min.
MS (ESI$^+$): m/z=376 [M+H]$^+$
$^1$H-NMR (300 MHz, DMSO-d$_6$): δ=9.45 (s, 1H), 8.0 (d, 1H), 7.35 (s, 1H), 7.3 (d, 1H), 7.2 (dd, 1H), 4.3 (q, 2H), 4.25 (d, 2H), 2.25 (s, 3H), 1.3 (tr, 3H), 1.25 (m, 1H), 0.55 (q, 2H), 0.35 (q, 2H) ppm.

Step 4

4-({[(4-Chloro-2-methylphenyl)amino]carbonyl}amino)-1-(cyclopropylmethyl)-1H-imidazole-2-carboxylic acid

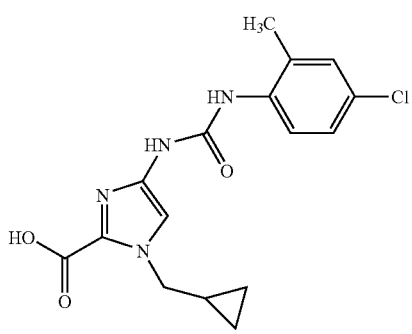

10.6 g (28.1 mmol) of ethyl 4-({[(4-chloro-2-methylphenyl)amino]carbonyl}amino)-1-(cyclopropylmethyl)-1H-imidazole-2-carboxylate are suspended in 158 ml of ethanol. With ice cooling, 16.4 ml of water and 6 ml (112 mmol) of a 50% aqueous sodium hydroxide solution are added. The reaction mixture is stirred at room temperature for 1 h and then concentrated in vacuo. The residue is taken up in 100 ml of isopropanol, and 100 ml of 1N hydrochloric acid are added with ice cooling. The crystals are collected by suction filtration and dried at 40° C. in vacuo.

Yield: 9.85 g (100% of theory)
LC-MS (Method 4): $R_t$=1.74 min.
MS (ESI$^+$): m/z=349 [M+H]$^+$
$^1$H-NMR (400 MHz, DMSO-d$_6$): δ=9.4 (s, 1H), 8.0 (d, 1H), 7.3 (s, 1H), 7.25 (d, 1H), 7.2 (dd, 1H), 4.25 (d, 2H), 2.25 (s, 3H), 1.25 (m, 1H), 0.55 (q, 2H), 0.35 (q, 2H) ppm.

Example 5A

1-(Cyclopropylmethyl)-4-[({[4-(trifluoromethoxy)phenyl]amino}carbonyl)amino]-1H-imidazole-2-carboxylic acid

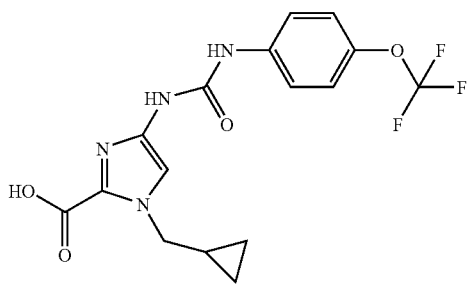

The preparation takes place in analogy to Example 4A.
Yield: 10.2 g (93% of theory)
LC-MS (Method 4): $R_t$=1.87 min.
MS (ESI$^+$): m/z=385 [M+H]$^+$
$^1$H-NMR (400 MHz, DMSO-d$_6$): δ=8.6 (s, 1H), 8.4 (s, 1H), 7.55 (d, 2H), 7.4 (s, 1H), 7.25 (d, 2H), 4.25 (d, 2H), 1.25 (m, 1H), 0.55 (q, 2H), 0.35 (q, 2H) ppm.

Example 6A

1-Butyl-4-({[(4-chloro-2-methylphenyl)amino]carbonyl}amino)-1H-imidazole-2-carboxylic acid

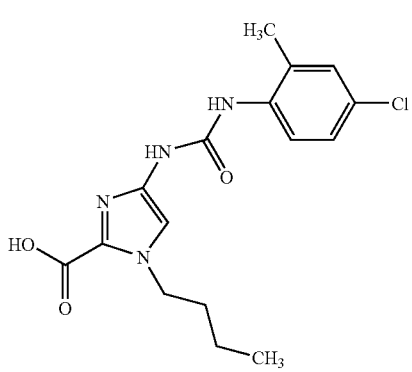

The preparation takes place in analogy to Example 4A.
Yield: 2.2 g (93% of theory)
LC-MS (Method 4): $R_t$=1.83 min.
MS (ESI$^+$): m/z=351 [M+H]$^+$
$^1$H-NMR (300 MHz, DMSO-d$_6$): δ=9.35 (s, 1H), 8.0 (d, 1H), 7.3 (s, 1H), 7.25 (d, 1H), 7.2 (dd, 1H), 4.35 (tr, 2H), 2.25 (s, 3H), 1.7 (quintet, 2H), 1.25 (sextet, 2H), 0.9 (tr, 3H) ppm.

Example 7A

1-Butyl-4-[({[4-(trifluoromethoxy)phenyl]amino}carbonyl)amino]-1H-imidazole-2-carboxylic acid

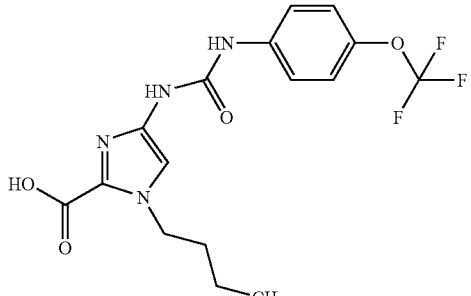

The preparation takes place in analogy to Example 4A.
Yield: 2.05 g (96% of theory)
LC-MS (Method 4): $R_t$=1.96 min.
MS (ESI$^+$): m/z=387 [M+H]$^+$
$^1$H-NMR (300 MHz, DMSO-d$_6$): δ=9.0 (s, 1H), 8.9 (s, 1H), 7.55 (d, 2H), 7.3 (s, 1H), 7.25 (d, 1H), 4.35 (tr, 2H), 1.7 (quintet, 2H), 1.25 (sextet, 2H), 0.9 (tr, 3H) ppm.

Example 8A

4-[({[4-(Trifluoromethoxy)phenyl]amino}carbonyl)amino]-1-[4-(trifluoromethyl)benzyl]-1H-imidazole-2-carboxylic acid

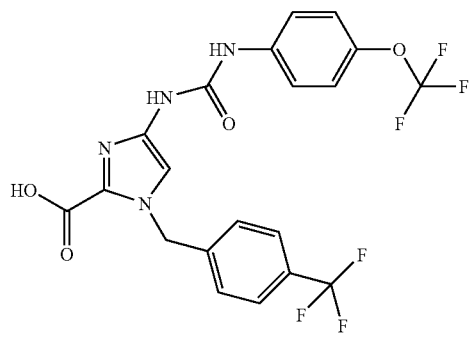

Preparation in analogy to Example 4A.

Yield: 15.2 g (100% of theory)

LC-MS (Method 2): $R_t$=2.46 min.

MS (ESI$^+$): m/z=489 [M+H]$^+$ $^1$H-NMR (300 MHz, DMSO-d$_6$): δ=9.15 (s, 1H), 9.05 (s, 1H), 7.75 (d, 2H), 7.55 (d, 2H), 7.45 (s, 1H), 7.35 (d, 2H), 7.25 (d, 2H), 5.7 (s, 2H) ppm.

Example 9A 4-({[4-Chloro-2-methylphenyl)amino]carbonyl}amino)-1-[4-(trifluoromethyl)benzyl]-1H-imidazole-2-carboxylic acid

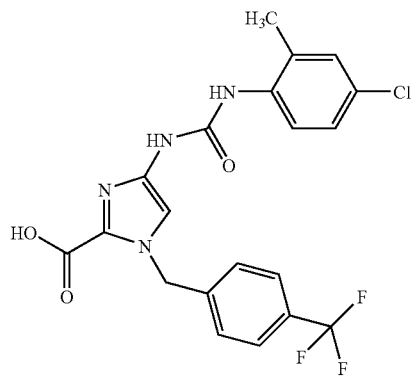

Preparation in analogy to Example 4A.

Yield: 15.6 g (100% of theory)

LC-MS (Method 4): $R_t$=2.23 min.

MS (ESI$^+$): m/z=453 [M+H]$^+$ $^1$H-NMR (300 MHz, DMSO-d$_6$): δ=9.5 (s, 1H), 7.95 (d, 1H), 7.75 (d, 2H), 7.4 (d, 2H), 7.35 (s, 1H), 7.25 (s, 1H), 7.15 (d, 1H), 5.75 (s, 2H), 2.25 (s, 3H) ppm.

Example 10A

Ethyl 1-methyl-4-nitro-1H-imidazole-2-carboxylate

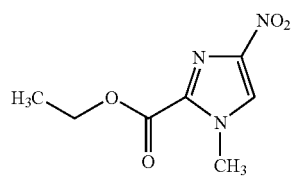

6.80 g (36.7 mmol) of ethyl 4-nitro-1H-imidazole-2-carboxylate are dissolved in 140 ml of acetone, and 11.2 g (80.8 mmol) of potassium carbonate and 4.57 ml (73.5 mmol) of iodomethane are added. The mixture is then stirred at 60° C. for 4 h. According to TLC (cyclohexane/ethyl acetate 2:1), the starting material has been converted completely. After cooling, the mixture is filtered, the residue is washed with dichloromethane and the filtrate is freed from the solvent. The solid obtained is dried in vacuo.

Yield: 7.0 g (95% of theory)

LC-MS (Method 5): $R_t$=1.40 min.

MS (ESI$^+$): m/z=200 [M+H]$^+$ $^1$H-NMR (400 MHz, DMSO-d$_6$): δ=8.64 (s, 1H), 4.35 (q, 2H), 3.99 (s, 3H), 1.34 (t, 3H).

Example 11A

Ethyl 4-amino-1-methyl-1H-imidazole-2-carboxylate

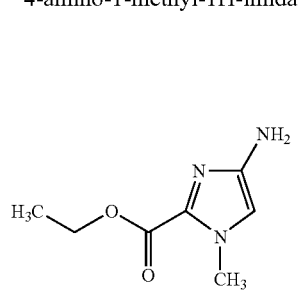

0.50 g (2.5 mmol) of ethyl 1-methyl-4-nitro-1H-imidazole-2-carboxylate are dissolved in 7.5 ml of ethanol, 0.13 g (0.13 mmol) of palladium-on-carbon (10%) are added and the mixture is hydrogenated at 3 bar for 12 h. The reaction solution is then filtered through kieselguhr and the filtrate is concentrated. The residue is dried in vacuo and reacted further without further purification.

Yield: 0.42 g (99% of theory)

LC-MS (Method 1): $R_t$=1.59 min.

MS (ESI$^+$): m/z=170 [M+H]$^+$ $^1$H-NMR (400 MHz, DMSO-d$_6$): δ=6.47 (s, 1H), 4.55 (bs, 2H), 4.19 (q, 2H), 3.80 (s, 3H), 1.28 (t, 3H).

Example 12A

Ethyl 1-methyl-4-[({[4-(trifluoromethoxy)phenyl]amino}carbonyl)amino]-1H-imidazole-2-carboxylate

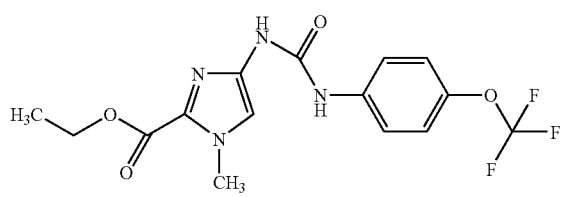

Under argon, 1.46 g (7.21 mmol) of 4-(trifluoromethoxy)phenyl isocyanate are added to 1.22 g (3.61 mmol) of ethyl 4-amino-1-methyl-1H-imidazole-2-carboxylate (synthesis in analogy to Example 4A step 3, or also according to Tetrahedron Lett. 2003, 44, 1607 and the literature cited therein) in 50 ml of THF, and the mixture is stirred at room temperature overnight. The reaction mixture is filtered and the filtrate is concentrated in vacuo and purified chromatographically.

Yield: 860 mg (62% of theory)
LC-MS (Method 5): $R_t$=2.41 min.
MS (ESI$^+$): m/z=373 [M+H]$^+$
$^1$H-NMR (300 MHz, DMSO-d$_6$): δ=8.98 (bs, 2H), 7.55 (m, 2H), 7.36 (s, 1H), 7.29 (m, 2H), 4.28 (q, 2H), 3.91 (s, 3H), 1.30 (t, 3H).

Example 13A

1-Methyl-4-[({[4-(trifluoromethoxy)phenyl]amino}carbonyl)amino]-1H-imidazole-2-carboxylic acid

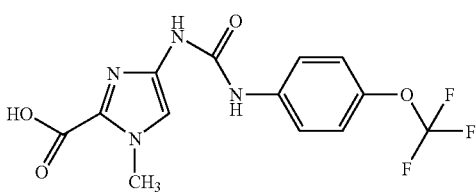

835 mg (2.13 mmol) of ethyl 1-methyl-4-[({[4-(trifluoromethoxy)phenyl]amino}carbonyl)amino]-1H-imidazole-2-carboxylate are suspended in 5 ml of ethanol and 12 ml of tetrahydrofuran. With ice cooling, 2 ml (25 mmol) of a 50% aqueous sodium hydroxide solution are added. The reaction mixture is stirred at room temperature overnight and then, with ice cooling, acidified with 1N hydrochloric acid. The solution is extracted with dichloromethane. The organic phase is concentrated in vacuo. The residue is purified by preparative HPLC.

Yield: 346 mg (44% of theory).
LC-MS (Method 4): $R_t$=1.62 min.
MS (ESI$^+$): m/z=345 [M+H]$^+$
$^1$H-NMR (400 MHz, DMSO-d$_6$): δ=9.33 (bs, 1H), 8.98 (bs, 1H), 7.55 (m, 2H), 7.30 (s, 1H), 7.28 (m, 2H), 3.90 (s, 3H).

Example 14A 1-(5-Methylpyridin-2-yl)piperazine

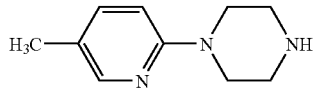

Step 1

1-(tert-Butyloxycarbonyl)-4-(5-methylpyridin-2-yl)piperazine

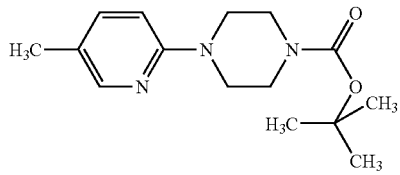

Under an argon atmosphere, 2.50 g (19.6 mmol) of 2-methyl-5-chloropyridine and 4.38 g (23.5 mmol) of N-(tert-butyloxycarbonyl)piperazine are dissolved in 50 ml of absolute toluene. 2.26 g (23.5 mmol) of sodium tert-butoxide, 0.37 g (0.59 mmol) of BINAP and 0.36 g (0.39 mmol) of tris(dibenzylideneacetone)dipalladium are then added, and the mixture is heated at 70° C. for 12 h. After cooling, diethyl ether is added to the reaction mixture, the mixture is washed three times with a saturated sodium chloride solution and dried over sodium sulfate and the solvent is removed in vacuo. The residue is purified by flash chromatography (cyclohexane/ethyl acetate 9:1).

Yield: 5.27 g (97% of theory).
LC-MS (Method 4): $R_t$=1.26 min.
MS (ESI$^+$): m/z=278 [M+H]$^+$
$^1$H-NMR (300 MHz, CDCl$_3$): δ=8.02 (d, 1H), 7.34 (dd, 1H), 6.59 (d, 1H), 3.55 (m, 4H), 3.45 (m, 4H), 2.21 (s, 3H), 1.49 (s, 9H).

Step 2

1-(5-Methylpyridin-2-yl)piperazine

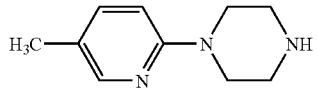

3.47 g (12.5 mmol) of 1-(tert-butyloxycarbonyl)-4-(5-methylpyridin-2-yl)piperazine are dissolved in 10 ml of dioxane, and 31 ml (125 mmol) of hydrogen chloride in dioxane (4 molar) are added. The mixture is stirred at RT for 2 h. The mixture is then concentrated and the residue is rendered alkaline using a 1M aqueous sodium hydroxide solution and extracted several times with dichloromethane. The combined organic phases are dried over sodium sulfate, concentrated and dried in vacuo.

Yield: 2.18 g (98% of theory).

LC-MS (Method 5): $R_t$=0.38 min.

MS (ESI$^+$): m/z=177 [M+H]$^+$ $^1$H-NMR (300 MHz, CDCl$_3$): δ=8.02 (d, 1H), 7.32 (dd, 1H), 6.59 (d, 1H), 3.45 (m, 4H), 3.00 (m, 4H), 2.20 (s, 3H).

Example 15A

1-Ethyl-4-[({[4-(trifluoromethoxy)phenyl]amino}carbonyl)amino]-1H-imidazole-2-carboxylic acid

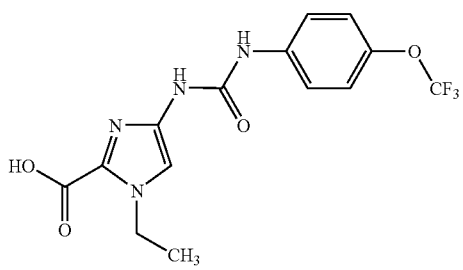

The preparation takes place in analogy to Example 13A.

Yield: 425 mg (91% of theory).

LC-MS (Method 5): $R_t$=1.94 min.

MS (ESI$^+$): m/z=359 [M+H]$^+$ $^1$H-NMR (300 MHz, DMSO-d$_6$): δ=10.3 (bs, 1H), 7.67 (m, 2H), 7.24 (s, 1H), 7.20 (m, 2H), 4.45 (q, 2H), 1.33 (t, 3H).

Example 16A

1-Butyl-4-[({[4-(trifluoromethyl)phenyl]amino}carbonyl)amino]-1H-imidazole-2-carboxylic acid

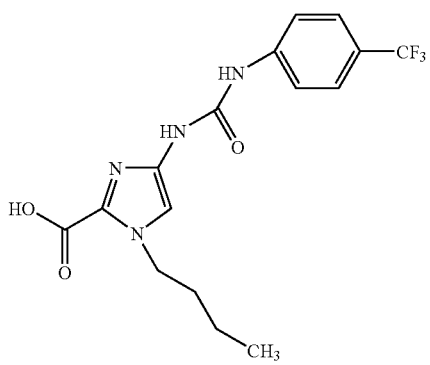

The preparation takes place in analogy to Example 13A.

Yield: 1.71 g (90% of theory)

LC-MS (Method 2): $R_t$=2.13 min.

MS (ESI$^+$): m/z=371 [M+H]$^+$ $^1$H-NMR (300 MHz, DMSO-d$_6$): δ=9.30 (bs, 1H), 9.03 (bs, 1H), 7.64 (m, 4H), 7.36 (s, 1H), 4.35 (t, 2H), 1.68 (quintet, 2H), 1.26 (sextet, 2H), 0.89 (t, 3H).

Example 17A 1-(5-Fluoropyridin-2-yl)piperazine

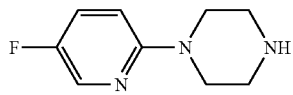

With stirring, 500 mg (2.84 mmol) of 2-bromo-5-fluoropyridine and 1.22 g (14.2 mmol) of piperazine are heated at 150° C. for 24 h. After cooling, excess piperazine is distilled off in vacuo (Kugelrohr, 1.5 mbar, 120° C.). The residue is purified by flash chromatography (dichloromethane/ethanol/conc. ammonia solution, 30:1:0.1).

Yield: 267 mg (52% of theory).

LC-MS (Method 9): $R_t$=8.07 min.

MS (DCI): m/z=182 [M+H]$^+$ $^1$H-NMR (400 MHz, DMSO-d$_6$): δ=8.07 (d, 1H), 7.48 (td, 1H), 6.82 (dd, 1H), 3.32 (t, 4H), 2.78 (t, 4H).

Example 18A 1-(5-Bromopyridin-2-yl)piperazine

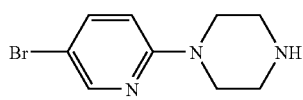

The preparation takes place in analogy to Example 17A.

Yield: 827 mg (81% of theory).

LC-MS (Method 1): $R_t$=2.02 min.

MS (ESI$^+$): m/z=242 [M+H]$^+$ $^1$H-NMR (300 MHz, DMSO-d$_6$): δ=8.15 (d, 1H), 7.65 (dd, 1H), 6.79 (d, 1H), 3.38 (m, 4H), 2.74 (m, 4H).

Example 19A 1-(5-Methoxypyridin-2-ylpiperazine

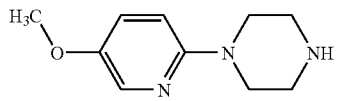

The preparation takes place in analogy to Example 14A.

Yield: 91 mg (90% of theory).

$^1$H-NMR (400 MHz, CDCl$_3$): δ=7.94 (d, 1H), 7.15 (dd, 1H), 6.64 (d, 1H), 3.80 (s, 3H), 3.48 (m, 4H), 3.00 (m, 4H).

Example 20A

4-[({[4-(Difluoromethoxy)phenyl]amino}carbonyl)amino]-1-methyl-1H-imidazole-2-carboxylic acid

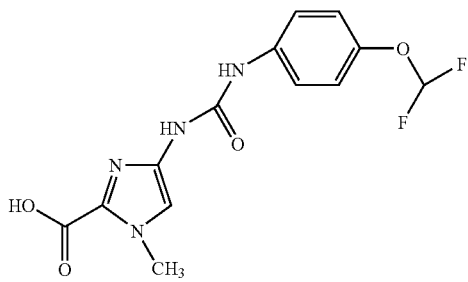

The preparation takes place in analogy to Example 13A.

Yield: 964 mg (81% of theory).

HPLC (Method 10): $R_t$=3.57 min.

MS (ESI$^+$): m/z=327 [M+H]$^+$ $^1$H-NMR (400 MHz, CDCl$_3$): δ=8.9 (s, 1H), 8.8 (s, 1H), 7.5 (d, 2H), 7.3 (s, 2H), 7.1 (t, 1H), 7.09 (d, 2H), 3.9 (s, 3H).

Example 21A

1-[(1-Ethyl-4-nitro-1H-imidazol-2-yl)carbonyl]-4-(pyridin-2-yl)piperazine

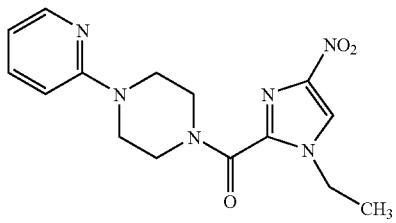

A mixture of 1.23 g (5.06 mmol) of ethyl 1-ethyl-4-nitro-1H-imidazole-2-carboxylate (prepared in analogy to Example 10A) and 2.48 g (15.2 mmol) of N-(pyridin-2-yl)piperazine is stirred at 100° C. overnight. For the work-up, the crude mixture obtained is purified by preparative HPLC. 0.724 g (43% of theory) of product are obtained.

HPLC (Method 10): $R_t$=3.19 min.

MS (ESI$^+$): m/z=331 [M+H]$^+$ $^1$H-NMR (300 MHz, DMSO-d$_6$): δ=8.7 (s, 1H), 8.1 (m, 1H), 7.55 (m, 1H), 6.9 (d, 1H), 6.65 (dd, 1H), 4.2 (q, 2H), 3.8 (m, 4H), 3.65 (m, 2H), 3.55 (m, 2H), 1.4 (t, 3H).

Example 22A

4-[({[4-(Difluoromethoxy)phenyl]amino}carbonyl)amino]-1-butyl-1H-imidazole-2-carboxylic acid

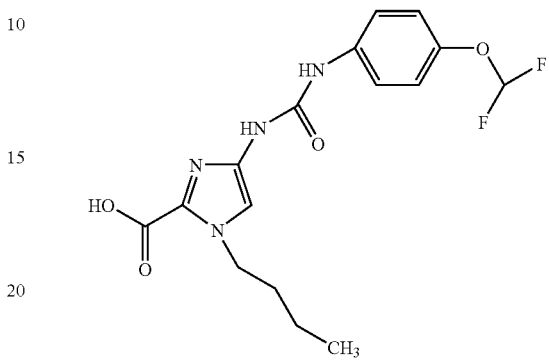

The preparation takes place in analogy to Example 13A.

Yield: 1.06 g (71% of theory).

HPLC (Method 10): $R_t$=4.046 min.

MS (ESI$^+$): m/z=369 [M+H]$^+$ $^1$H-NMR (400 MHz, CDCl$_3$): δ=11.1 (s, 1H), 7.7 (d, 2H), 7.1 (t, 1H), 7.05 (m, 3H), 4.5 (t, 2H), 1.7 (m, 2H), 1.3 (m, 2H), 0.9 (t, 3H).

Example 23A

1-[(1-Methyl-4-nitro-1H-imidazol-2-yl)carbonyl]-4-(pyridin-2-yl)piperazine

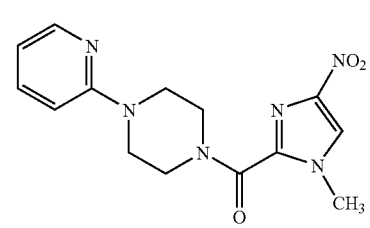

The preparation takes place in analogy to Example 21A.

Yield: 4 g (72% of theory)

HPLC (Method 10): $R_t$=2.99 min.

MS (ESI$^+$): m/z=317 [M+H]$^+$ $^1$H-NMR (300 MHz, DMSO-d$_6$): δ=8.6 (s, 1H), 8.15 (m, 1H), 7.55 (m, 1H), 6.9 (d, 1H), 6.7 (dd, 1H), 3.9 (m, 5H), 3.8 (m, 2H), 3.7-3.5 (m, 4H).

Example 24A

1-Methyl-4-[({[4-(trifluoromethyl)phenyl]amino}carbonyl)amino]-1H-imidazole-2-carboxylic acid

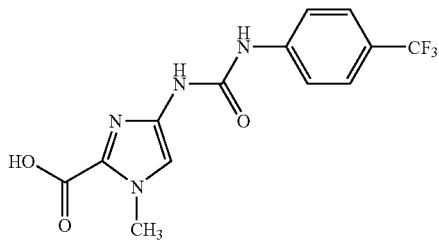

The preparation takes place in analogy to Example 13A.

Yield: 168 mg (99% of theory).

HPLC (Method 4): $R_t$=1.57 min.

MS (ESI$^+$): m/z=329 [M+H]$^+$ $^1$H-NMR (400 MHz, CDCl$_3$): δ=9.80 (bs, 1H), 9.18 (bs, 1H), 7.65 (m, 4H), 7.48 (s, 1H), 3.92 (s, 3H).

Exemplary Embodiments

Example 1

N-{1-Methyl-2-[(4-pyridin-2-ylpiperazin-1-yl)carbonyl]-1H-imidazol-4-yl}-N'-[4-(trifluoromethoxy)phenyl]urea

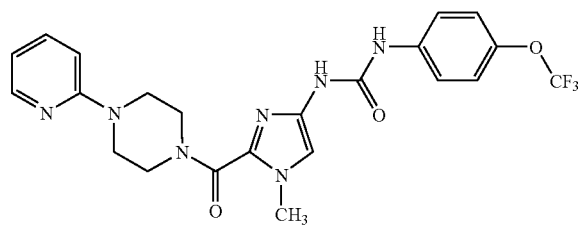

1.50 g (4.36 mmol) of Example 13A are dissolved in 30 ml of DMF, and 1.82 g (5.66 mmol) of O-(benzotriazol-1-yl)-N,N,N',N'-tetramethyluronium tetrafluoroborate (TBTU) and 266 mg (2.18 mmol) of 4-dimethylaminopyridine are added. After the addition of 925 mg (5.66 mmol) of 1-(pyridin-2-yl)piperazine, the mixture is stirred at RT for 4 h. The reaction mixture is purified by RP-HPLC.

Yield: 1.79 g (83% of theory).

LC-MS (Method 2): $R_t$=1.83 min.

MS (ESI$^+$): m/z=490 [M+H]$^+$ $^1$H-NMR (400 MHz, DMSO-d$_6$): δ=8.89 (bs, 2H), 8.12 (d, 1H), 7.55 (m, 3H), 7.29 (m, 2H), 7.20 (s, 1H), 6.88 (d, 1H), 6.68 (dd, 1H), 4.02 (bs, 2H), 3.77 (s, 3H), 3.71 (bs, 2H), 3.58 (bs, 4H).

Example 2

N-(1-Methyl-2-{[4-(5-methylpyridin-2-yl)piperazin-1-yl]carbonyl}-1H-imidazol-4-yl)-N'-[4-(trifluoromethoxy)phenyl]urea

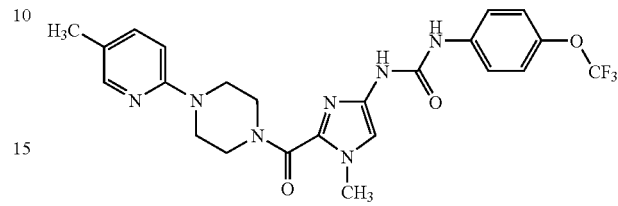

100 mg (0.29 mmol) of Example 13A are dissolved in 2 ml of DMF, and 139 mg (0.44 mmol) of O-(benzotriazol-1-yl)-N,N,N',N'-tetramethyluronium tetrafluoroborate (TBTU) and 53 mg (0.44 mmol) of 4-dimethylaminopyridine are added. After the addition of 103 mg (0.58 mmol) of Example 14A, the mixture is stirred at RT for 4 h. The reaction mixture is purified by RP-HPLC.

Yield: 103 mg (70% of theory).

LC-MS (Method 5): $R_t$=2.01 min.

MS (ESI$^+$): m/z=504 [M+H]$^+$ $^1$H-NMR (300 MHz, DMSO-d$_6$): δ=8.92 (bs, 2H), 7.99 (d, 1H), 7.54 (m, 2H), 7.42 (dd, 1H), 7.28 (m, 2H), 7.20 (s, 1H), 6.80 (d, 1H), 4.00 (bs, 2H), 3.77 (s, 3H), 3.72 (bs, 2H), 3.51 (bs, 4H), 2.16 (s, 3H).

Example 3

N-(2-{[4-(5-Chloropyridin-2-yl)piperazin-1-yl]carbonyl}-1-ethyl-1H-imidazol-4-yl)-N'-[4-(trifluoromethoxy)phenyl]urea

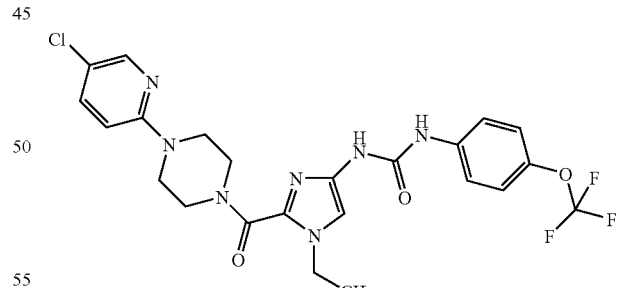

The preparation takes place in analogy to Example 2.

Yield: 55 mg (68% of theory).

LC-MS (Method 5): $R_t$=2.76 min.

MS (ESI$^+$): m/z=538 [M+H]$^+$ $^1$H-NMR (300 MHz, DMSO-d$_6$): δ=8.97 (bs, 1H), 8.92 (bs, 1H), 8.14 (d, 1H), 7.65 (dd, 1H), 7.54 (m, 2H), 7.28 (m, 2H), 7.24 (s, 1H), 6.92 (d, 1H), 4.16 (q, 2H), 3.97 (bs, 2H), 3.72 (bs, 2H), 3.59 (bs, 4H), 1.32 (t, 3H).

Example 4

N-(2-{[4-(4-Methoxyphenyl)piperazin-1-yl]carbonyl}-1-methyl-1H-imidazol-4-yl)-N'-[4-(trifluoromethoxy)phenyl]urea

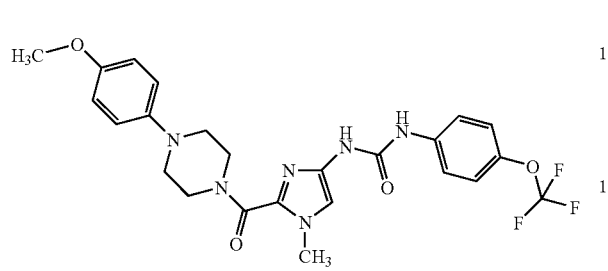

The preparation takes place in analogy to Example 2.

Yield: 35 mg (58% of theory).

LC-MS (Method 4): $R_t$=2.24 min.

MS (ESI$^+$): m/z=519 [M+H]$^+$ $^1$H-NMR (400 MHz, DMSO-d$_6$): δ=8.89 (bs, 2H), 7.53 (m, 2H), 7.28 (m, 2H), 7.19 (s, 1H), 6.92 (m, 2H), 6.84 (m, 2H), 4.05 (bs, 2H), 3.75 (m, 5H), 3.69 (s, 3H), 3.08 (bs, 4H).

Example 5

N-[4-(Difluoromethoxy)phenyl]-N'-(1-methyl-2-{[4-(5-methylpyridin-2-yl)piperazin-1-yl]-carbonyl}-1H-imidazol-4-yl)urea

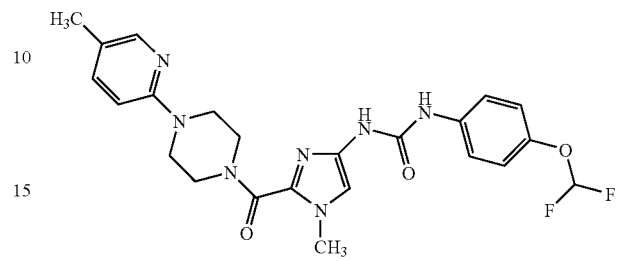

The preparation takes place in analogy to Example 2 from Example 20A.

Yield: 17 mg (29% of theory).

LC-MS (Method 5): $R_t$=1.70 min.

MS (ESI$^+$): m/z=486 [M+H]$^+$ $^1$H-NMR (400 MHz, DMSO-d$_6$): δ=8.84 (bs, 1H), 8.77 (bs, 1H), 7.98 (d, 1H), 7.47 (m, 2H), 7.42 (dd, 1H), 7.18 (s, 1H), 7.11 (t, 1H), 7.10 (m, 2H), 6.80 (d, 1H), 4.01 (bs, 2H), 3.77 (s, 3H), 3.71 (bs, 2H), 3.50 (bs, 4H), 2.16 (s, 3H).

The examples of Table 1 are prepared in analogy to Example 2.

TABLE 1

| Ex. No. | Structure | Molar mass | MS (ESI) [M + H]$^+$ | LC-MS $R_t$ [min] (method) | Starting compound | Yield (% of theory) |
|---|---|---|---|---|---|---|
| 6 | 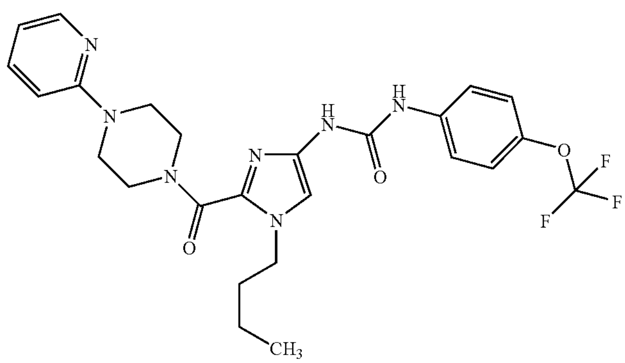 | 531.536 | 532 | 2.00 (4) | Example 7A | 67 |
| 7 | 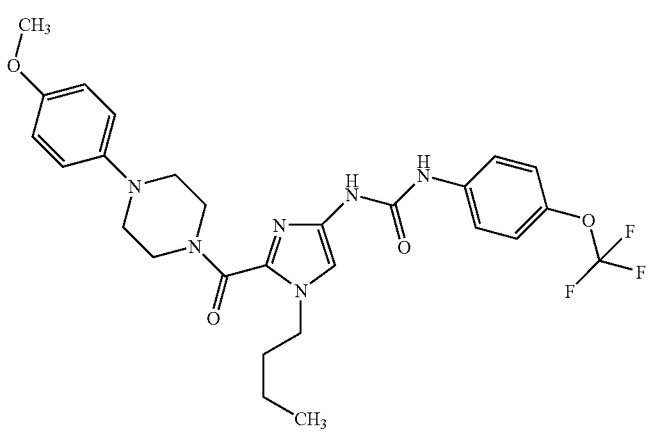 | 560.574 | 561 | 2.60 (4) | Example 7A | 72 |

TABLE 1-continued

| Ex. No. | Structure | Molar mass | MS (ESI) [M + H]+ | LC-MS R<sub>t</sub> [min] (method) | Starting compound | Yield (% of theory) |
|---|---|---|---|---|---|---|
| 8 | 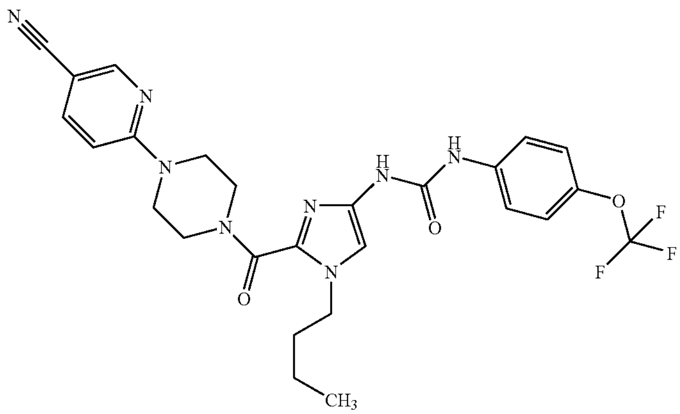 | 556.546 | 557 | 2.70 (2) | Example 7A | 60 |
| 9 | 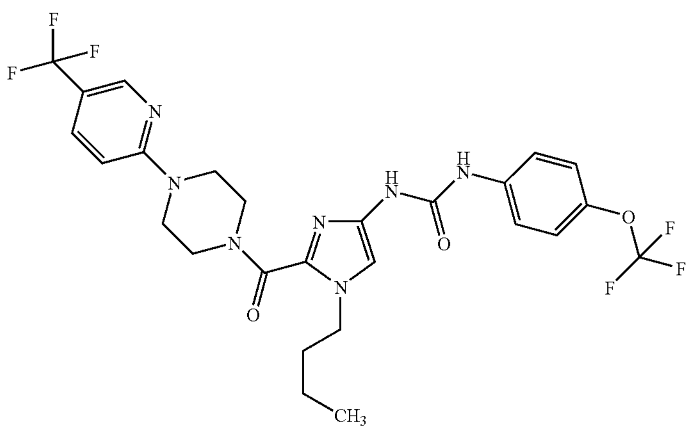 | 599.533 | 600 | 3.00 (5) | Example 7A | 57 |
| 10 | 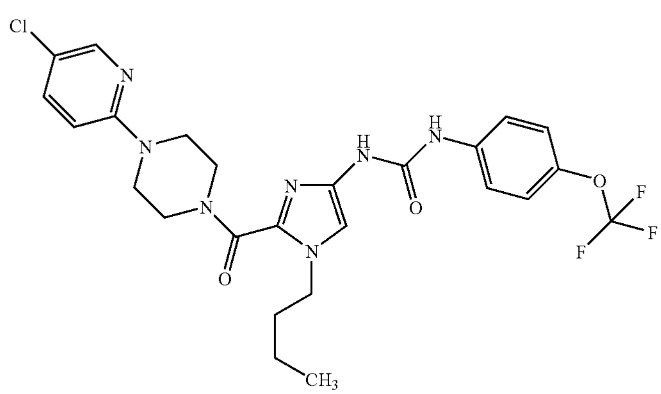 | 565.981 | 566 | 2.94 (5) | Example 7A | 72 |

TABLE 1-continued
| Ex. No. | Structure | Molar mass | MS (ESI) [M + H]+ | LC-MS Rt [min] (method) | Starting compound | Yield (% of theory) |
|---|---|---|---|---|---|---|
| 11 | 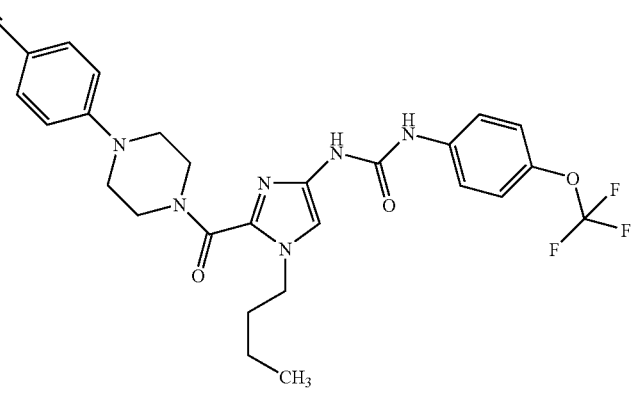 | 555.558 | 556 | 2.77 (2) | Example 7A | 62 |
| 12 | 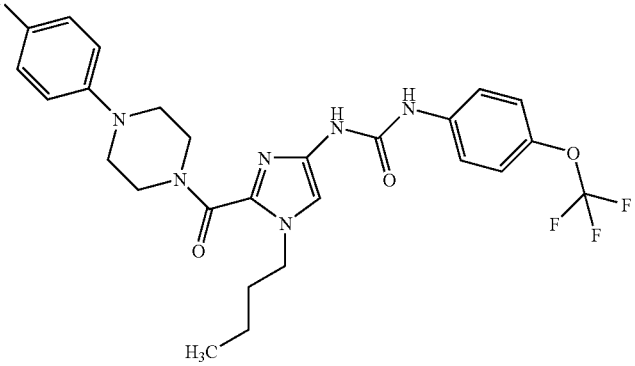 | 564.993 | 565 | 3.06 (5) | Example 7A | 51 |
| 13 | 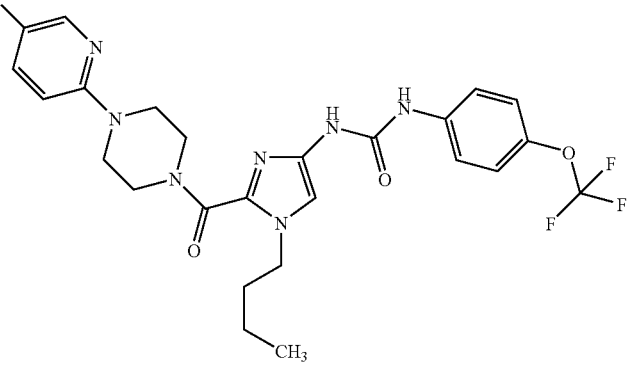 | 545.563 | 546 | 2.16 (5) | Example 7A | 42 |

TABLE 1-continued

| Ex. No. | Structure | Molar mass | MS (ESI) [M + H]+ | LC-MS $R_t$ [min] (method) | Starting compound | Yield (% of theory) |
|---|---|---|---|---|---|---|
| 14 | 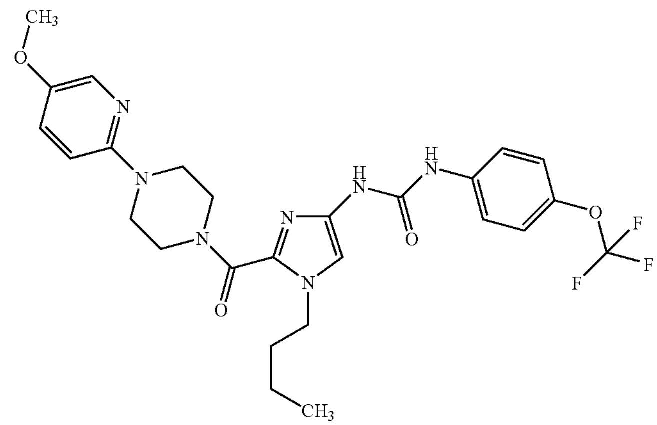 | 561.562 | 562 | 2.55 (5) | Example 7A | 72 |
| 15 | 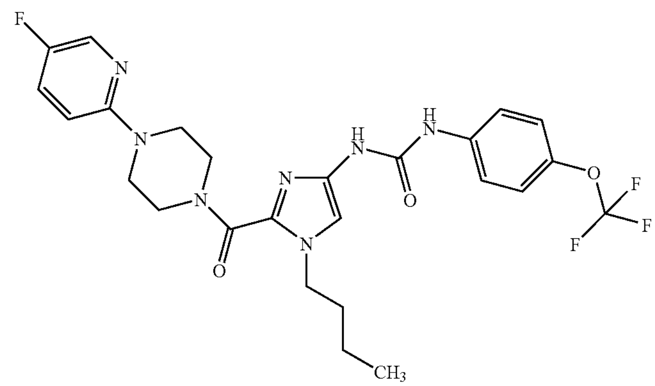 | 549.526 | 550 | 2.65 (4) | Example 7A Example 17A | 40 |
| 16 | 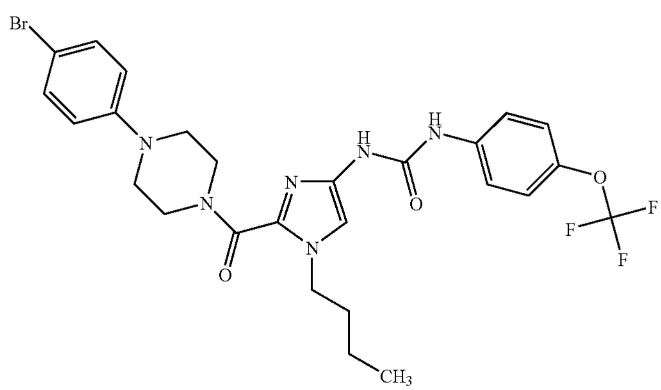 | 609.444 | 609 | 2.88 (4) | Example 7A | 77 |
| 17 | 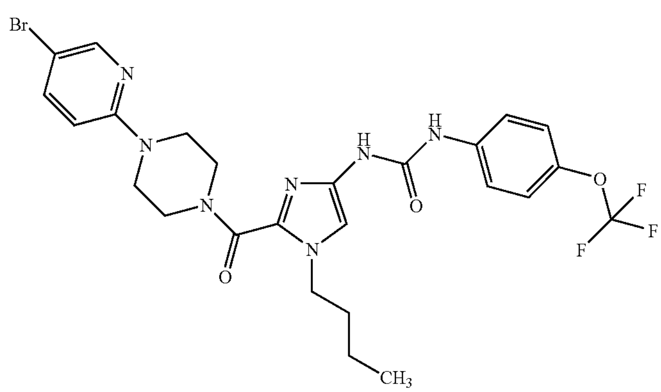 | 610.432 | 610 | 2.78 (4) | Example 7A | 81 |

TABLE 1-continued

| Ex. No. | Structure | Molar mass | MS (ESI) [M + H]+ | LC-MS R<sub>t</sub> [min] (method) | Starting compound | Yield (% of theory) |
|---|---|---|---|---|---|---|
| 18 | 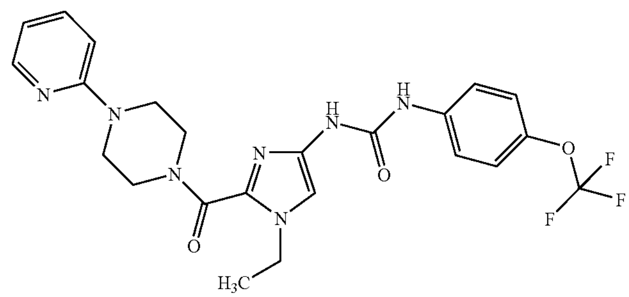 | 503.483 | 504 | 1.72 (4) | Example 15A | 47 |
| 19 | 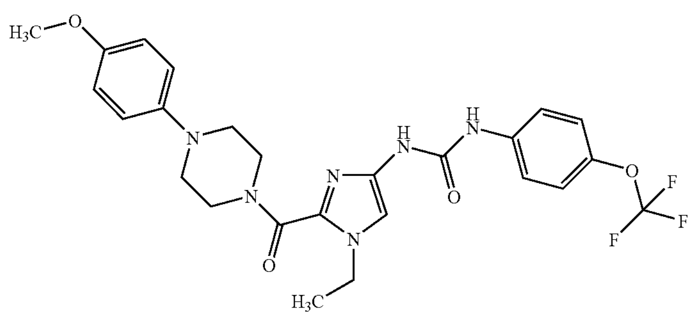 | 532.52 | 533 | 2.36 (4) | Example 15A | 72 |
| 20 | 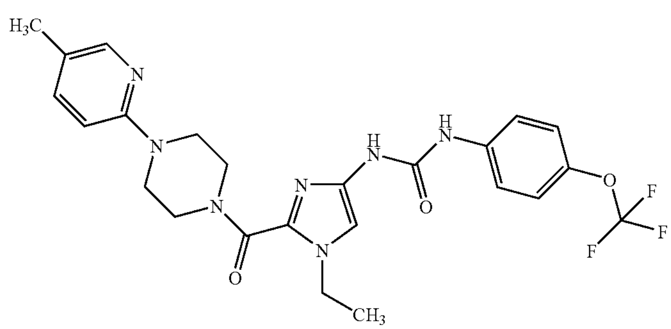 | 517.509 | 518 | 1.94 (5) | Example 15A | 22 |
| 21 | 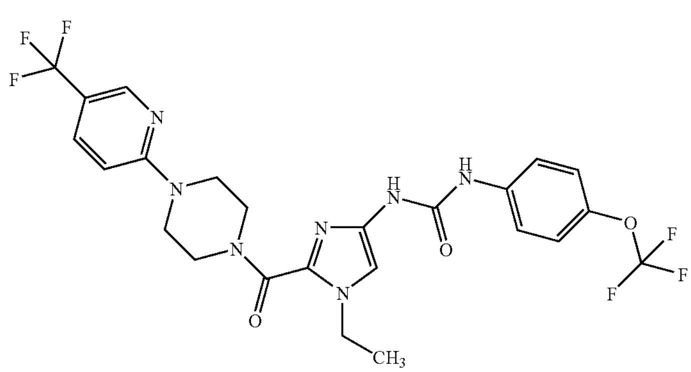 | 571.48 | 572 | 2.80 (5) | Example 15A | 28 |

TABLE 1-continued

| Ex. No. | Structure | Molar mass | MS (ESI) [M + H]+ | LC-MS R_t [min] (method) | Starting compound | Yield (% of theory) |
|---|---|---|---|---|---|---|
| 22 | 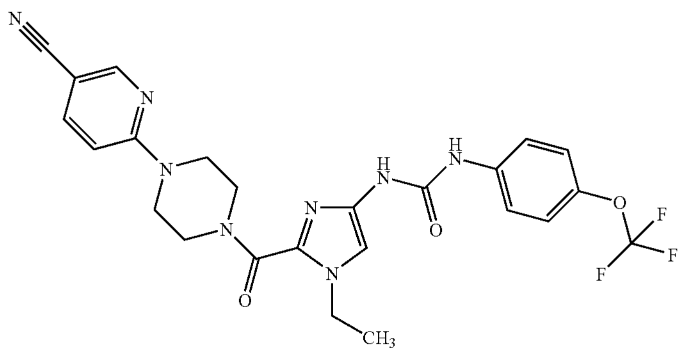 | 528.493 | 529 | 2.55 (5) | Example 15A | 70 |
| 23 | 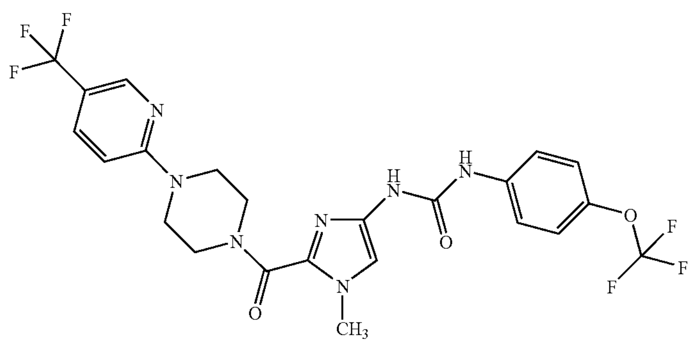 | 557.453 | 558 | 2.75 (5) | Example 13A | 79 |
| 24 | 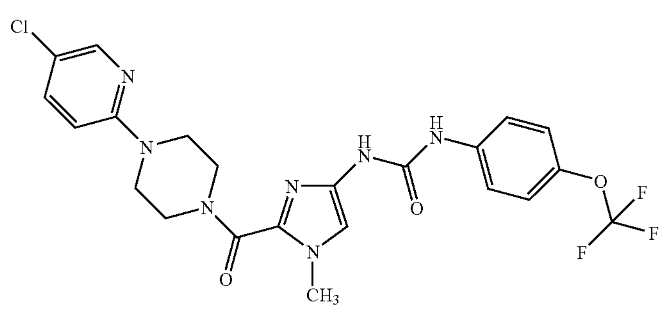 | 523.901 | 524 | 2.67 (5) | Example 13A | 50 |
| 25 | 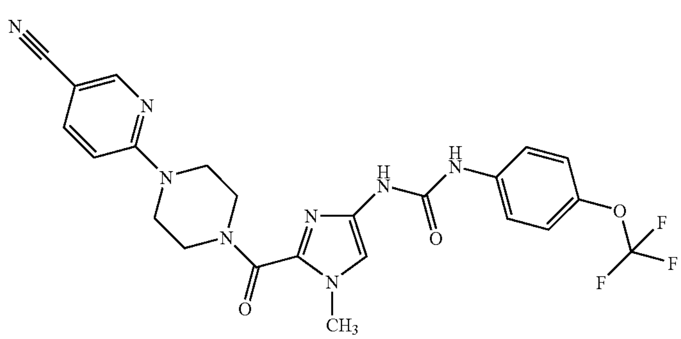 | 514.466 | 515 | 2.45 (5) | Example 13A | 74 |

TABLE 1-continued

| Ex. No. | Structure | Molar mass | MS (ESI) [M + H]+ | LC-MS R, [min] (method) | Starting compound | Yield (% of theory) |
|---|---|---|---|---|---|---|
| 26 | 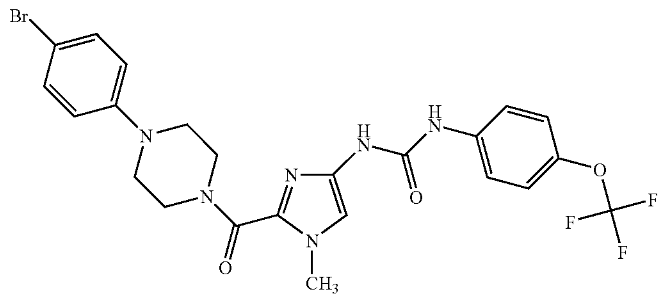 | 567.364 | 567 | 2.58 (4) | Example 13A | 52 |
| 27 | 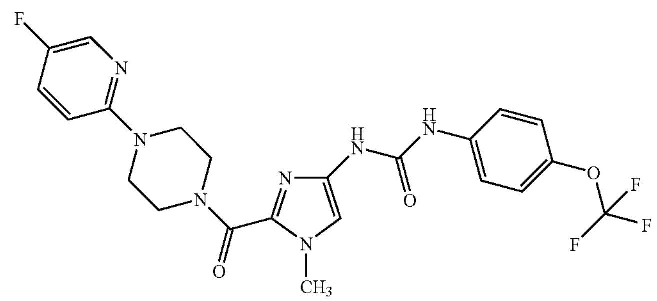 | 507.446 | 508 | 2.26 (4) | Example 13A Example 17A | 37 |
| 28 | 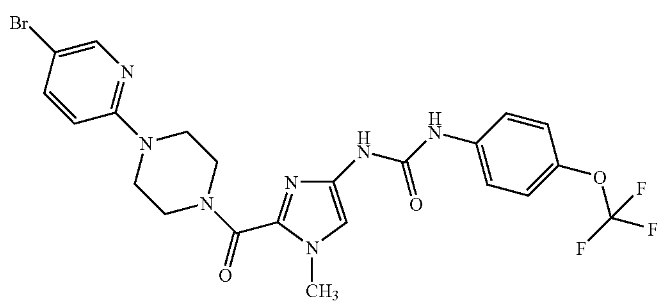 | 568.352 | 568 | 2.46 (4) | Example 13A | 71 |
| 29 | 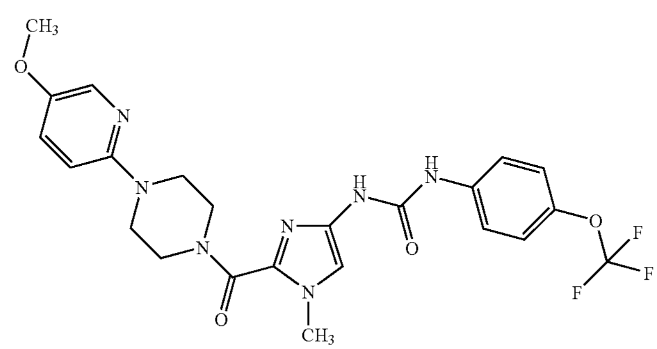 | 519.482 | 520 | 2.18 (5) | Example 13A | 72 |

TABLE 1-continued

| Ex. No. | Structure | Molar mass | MS (ESI) [M + H]+ | LC-MS $R_t$ [min] (method) | Starting compound | Yield (% of theory) |
|---|---|---|---|---|---|---|
| 30 | 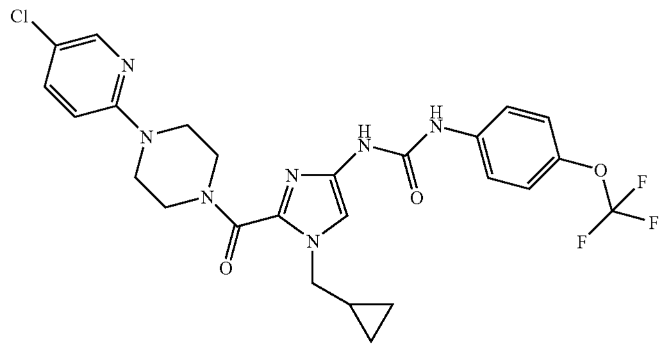 | 563.966 | 564 | 2.65 (4) | Example 5A | 50 |
| 31 | 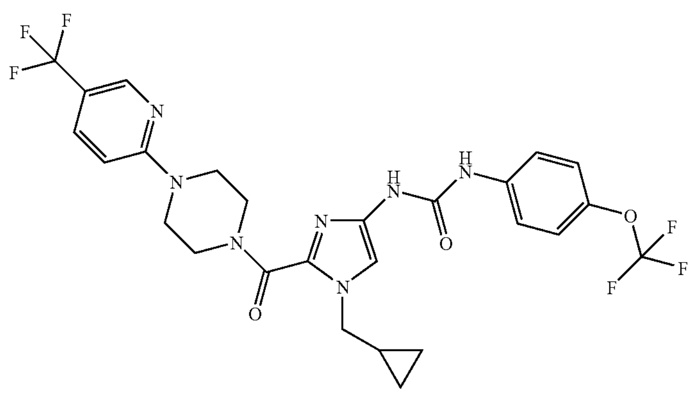 | 597.518 | 598 | 2.94 (5) | Example 5A | 48 |
| 32 | 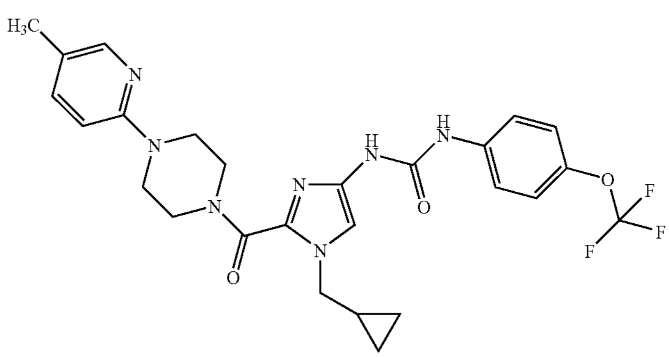 | 543.547 | 544 | 2.11 (5) | Example 5A | 59 |
| 33 | 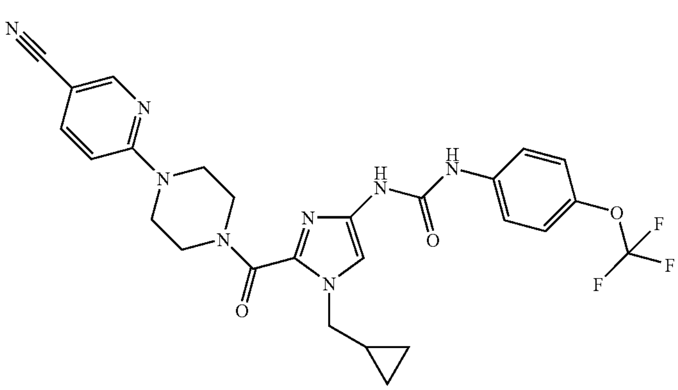 | 554.531 | 555 | 2.66 (5) | Example 5A | 51 |

TABLE 1-continued

| Ex. No. | Structure | Molar mass | MS (ESI) [M + H]+ | LC-MS R<sub>t</sub> [min] (method) | Starting compound | Yield (% of theory) |
|---|---|---|---|---|---|---|
| 34 | 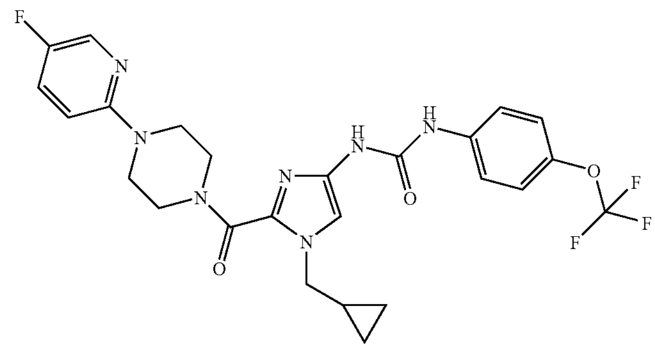 | 547.51 | 548 | 2.49 (4) | Example 5A Example 17A | 37 |
| 35 | 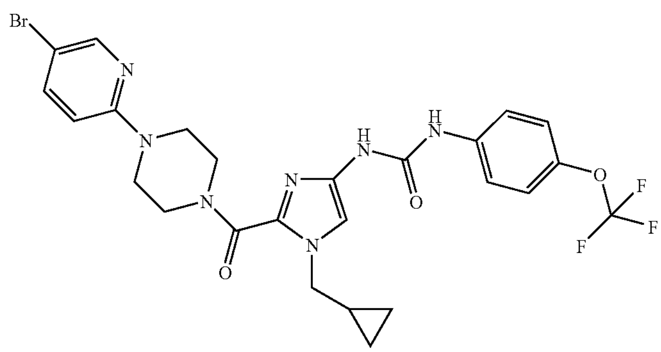 | 608.417 | 608 | 2.69 (4) | Example 5A | 86 |
| 36 | 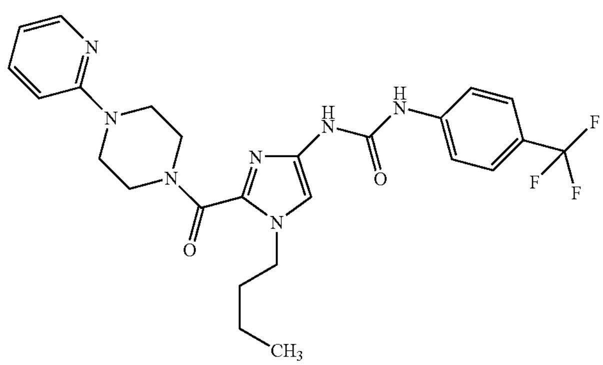 | 515.537 | 516 | 2.13 (2) | Example 16A | 79 |
| 37 | 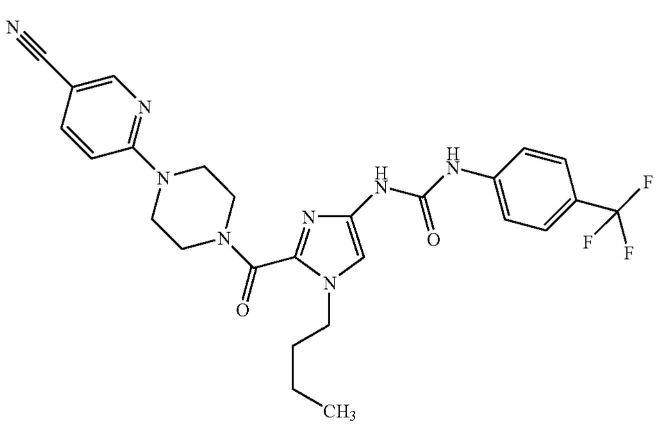 | 540.547 | 541 | 2.69 (2) | Example 16A | 65 |

TABLE 1-continued

| Ex. No. | Structure | Molar mass | MS (ESI) [M + H]+ | LC-MS R, [min] (method) | Starting compound | Yield (% of theory) |
|---|---|---|---|---|---|---|
| 38 | 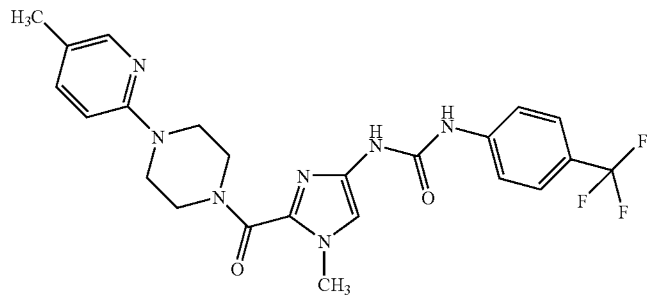 | 487.49 | 488 | 1.90 (5) | Example 24A | 71 |
| 39 | 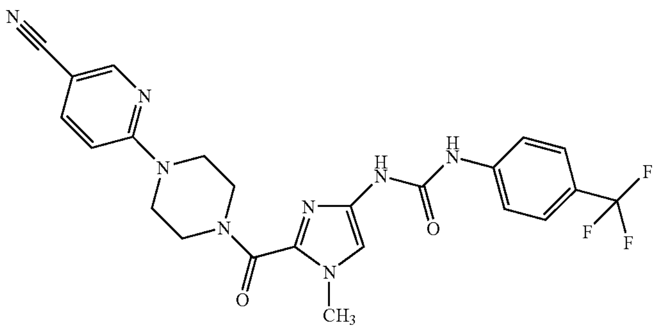 | 498.47 | 499 | 2.50 (5) | Example 24A | 43 |

Example 40

N-{1-(Cyclopropylmethyl)-2-[(4-pyridin-2-ylpiperazin-1-yl)carbonyl]-1H-imidazol-4-yl}-N'-[4-(trifluoromethoxy)phenyl]urea

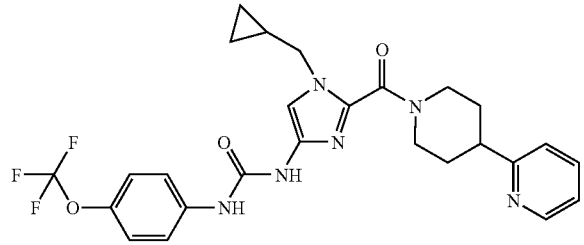

57.6 mg (0.15 mmol) of Example 5A are dissolved in 0.5 ml of DMF, and 59.5 mg (0.15 mmol) of O-(benzotriazol-1-yl)-N,N,N',N'-tetramethyluronium hexafluorophosphate (HBTU) and 15 mg (0.15 mmol) of triethylamine are added. After the addition of 49 mg (0.3 mmol) of N-(2-pyridyl)piperazine, the mixture is stirred at RT for 16 h. The reaction mixture is purified by RP-HPLC.

Yield: 46 mg (58% of theory).

LC-MS (Method 5): $R_t$=2.08 min.

MS (ESI+): m/z=530 [M+H]+

$^1$H-NMR (300 MHz, DMSO-$d_6$): δ=8.9 (s, 2H), 8.15 (d, 1H), 7.6-7.5 (m, 3H), 7.25 (m, 3H), 6.85 (d, 1H), 6.7 (dd, 1H), 4.05 (d, 2H), 4.00 (bs, 2H), 3.75 (bs, 2H), 3.6-3.5 (m, 4H), 1.75 (m, 1H), 0.5 (q, 2H), 0.35 (q, 2H).

The examples of Table 2 are prepared in analogy to Example 40.

TABLE 2

| Ex. No. | Structure | Molar mass | MS (EI) [M + H]+ | LC-MS R, [min] (method) | Starting compound | Yield [mg] (% of theory) |
|---|---|---|---|---|---|---|
| 41 | 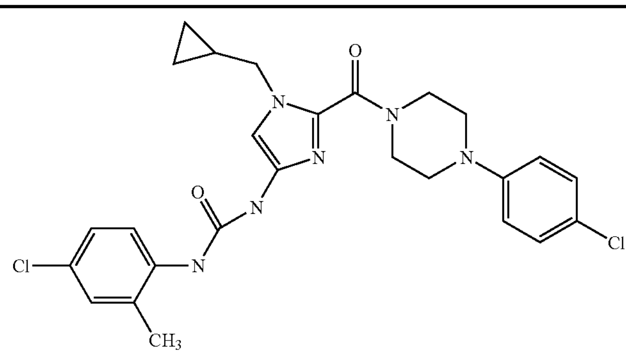 | 527.458 | 527 | 2.9 (2) | Example 4A | 43.6 (49) |

TABLE 2-continued

| Ex. No. | Structure | Molar mass | MS (EI) [M + H]⁺ | LC-MS R_t [min] (method) | Starting compound | Yield [mg] (% of theory) |
|---|---|---|---|---|---|---|
| 42 | 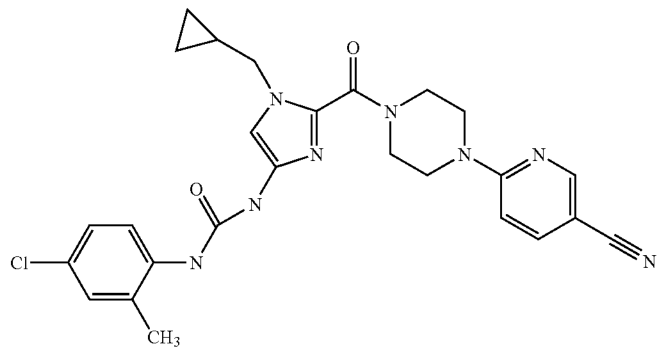 | 519.01 | 519 | 2.55 (2) | Example 4A | 23.3 (30) |
| 43 | 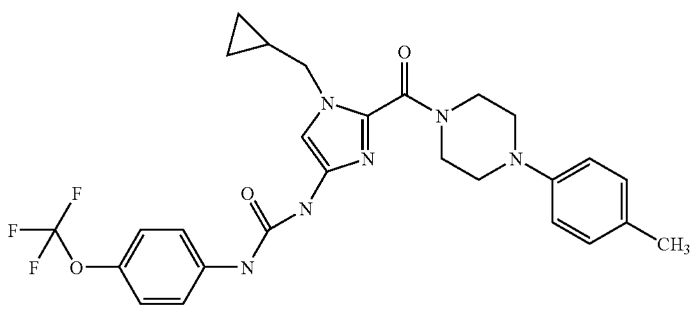 | 542.566 | 543 | 2.88 (2) | Example 5A | 21.6 (24) |
| 44 | 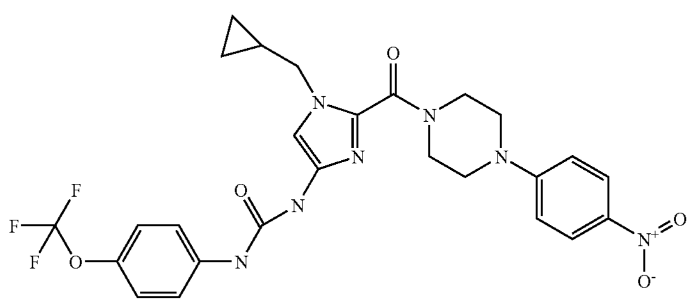 | 573.536 | 574 | 2.75 (2) | Example 5A | 24.4 (26) |
| 45 | 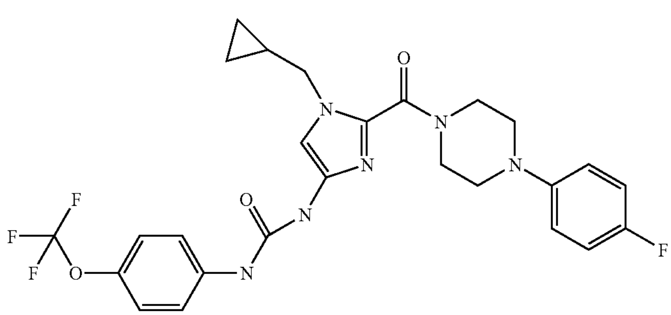 | 546.529 | 547 | 2.8 (2) | Example 5A | 28.5 (33) |

TABLE 2-continued
| Ex. No. | Structure | Molar mass | MS (EI) [M + H]+ | LC-MS R_t [min] (method) | Starting compound | Yield [mg] (% of theory) |
|---|---|---|---|---|---|---|
| 46 | 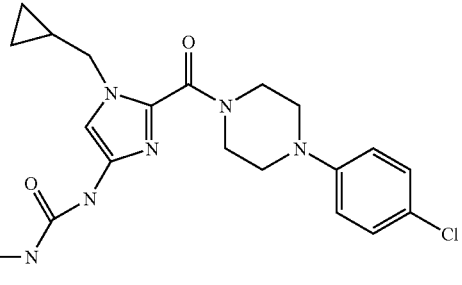 | 562.984 | 563 | 2.95 (2) | Example 5A | 42.4 (47) |
| 47 | 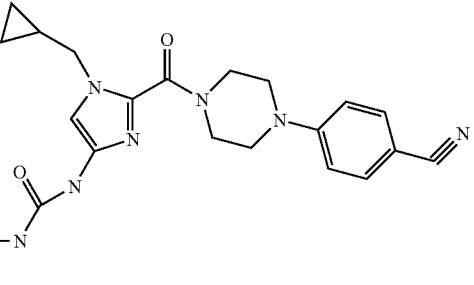 | 553.549 | 554 | 2.7 (2) | Example 5A | 9.2 (9) |
| 48 | 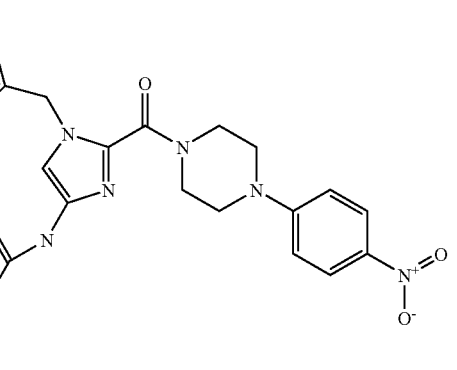 | 642.042 | 642 | 2.93 (2) | Example 9A | 25.2 (21) |
| 49 | 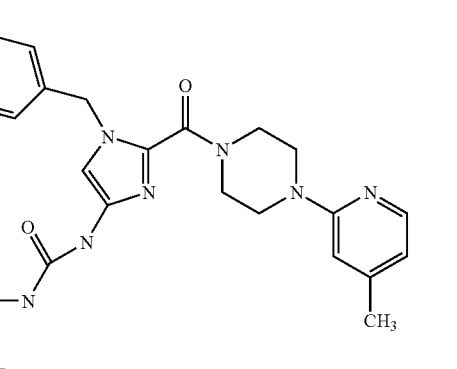 | 612.06 | 612 | 2.3 (2) | Example 9A | 2.1 (2) |

TABLE 2-continued

| Ex. No. | Structure | Molar mass | MS (EI) [M + H]+ | LC-MS $R_t$ [min] (method) | Starting compound | Yield [mg] (% of theory) |
|---|---|---|---|---|---|---|
| 50 | 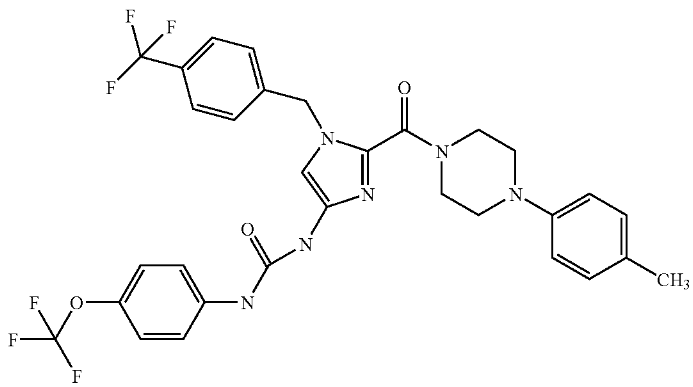 | 646.598 | 647 | 3.09 (2) | Example 8A | 36.4 (38) |
| 51 | 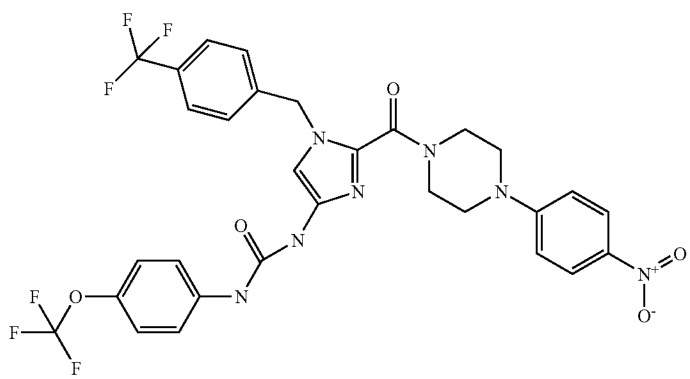 | 677.568 | 678 | 2.97 (2) | Example 8A | 16.3 (15) |

Example 52

N-(3,5-Difluorophenyl)-N'-{1-ethyl-2-[(4-pyridin-2-ylpiperazin-1-yl)carbonyl]-1H-imidazol-4-yl}urea

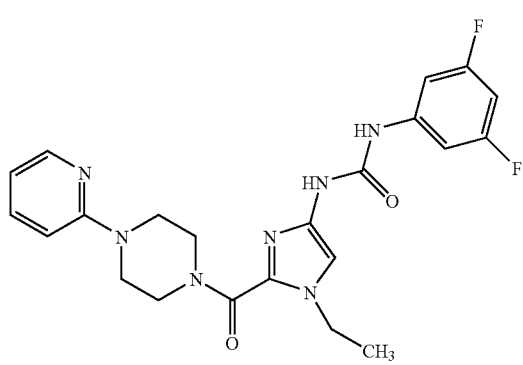

Firstly, a spatula tip of Raney nickel and then 11 mg (0.23 mmol) of hydrazine hydrate are added to a solution of 50 mg (0.15 mmol) of 1-[(1-ethyl-4-nitro-1H-imidazol-2-yl)carbonyl]-4-(pyridin-2-yl)piperazine in 6 ml of absolute THF, and the mixture is then stirred for 1 h. Sodium sulfate is added to the crude solution, which is then filtered through kieselguhr, and the filtercake is washed with methylene chloride. The filtrate is concentrated in vacuo and taken up again in 6 ml of THF, 28 mg (0.18 mmol) of difluorophenyl isocyanate and 2 mg of 1,4-diazabicyclo[2.2.2]octane are added and the mixture is stirred at room temperature. After 1 h, the solvent is removed on a rotary evaporator and the residue is purified by preparative HPLC. 20 mg (29% of theory) of product are obtained.

HPLC (Method 10): $R_t$=3.94 min.

MS (ESI+): m/z=456 [M+H]+

$^1$H-NMR (300 MHz, DMSO-d$_6$): δ=8.5 (2s, 2H), 8.1 (m, 1H), 7.55 (m, 1H), 7.25 (s, 1H), 1.15 (m, 2H), 6.9-6.65 (m, 3H), 4.2 (q, 2H), 3.9 (m, 2H), 3.7 (m, 2H), 3.55 (m, 4H), 1.3 (t, 3H).

The examples of Table 3 are prepared in analogy to Example 52, except for Example 57, which is prepared in analogy to Example 2.

TABLE 3

| Ex. No. | Structure | Molar mass | MS (ESI) [M + H]+ | HPLC R_t [min] (method 10) | Starting compound | Yield [mg] (% of theory) |
|---|---|---|---|---|---|---|
| 53 | 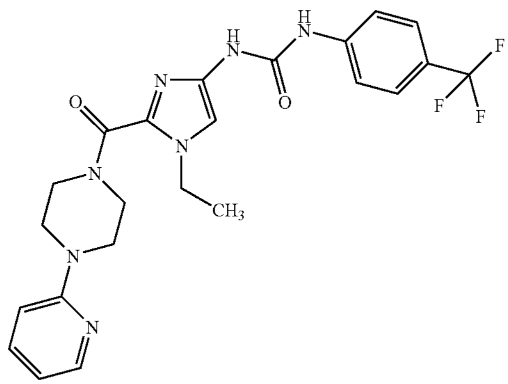 | 487.48 | 488 | 4.118 | Example 21A | 40 (51) |
| 54 | 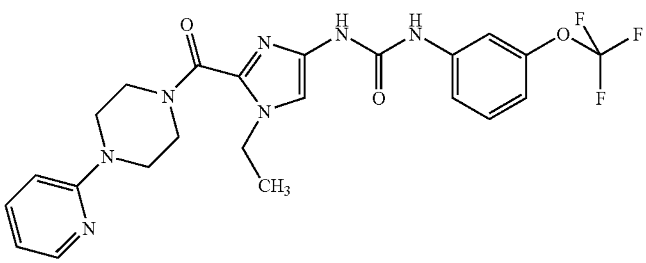 | 503.48 | 504 | 4.175 | Example 21A | 45 (57) |
| 55 | 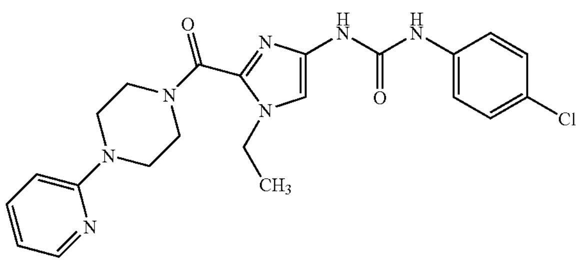 | 453.93 | 454 | 3.937 | Example 21A | 43 (63) |
| 56 | 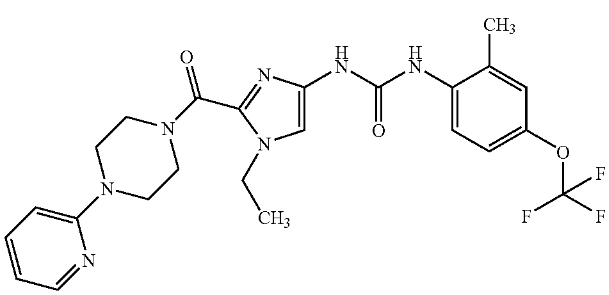 | 517.51 | 518 | 4.182 | Example 21A | 35 (45) |
| 57 | 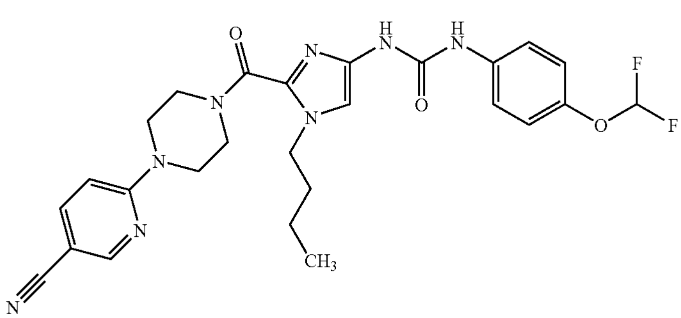 | 538.56 | 539 | 4.588 | Example 22A | 40 (82) |

TABLE 3-continued

| Ex. No. | Structure | Molar mass | MS (ESI) [M + H]+ | HPLC R$_t$ [min] (method 10) | Starting compound | Yield [mg] (% of theory) |
|---|---|---|---|---|---|---|
| 58 | 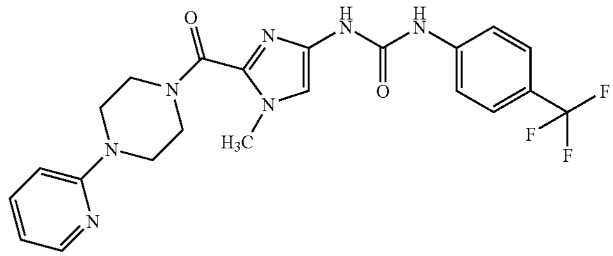 | 473.46 | 474 | 4.014 | Example 23A | 40 (53) |
| 59 | 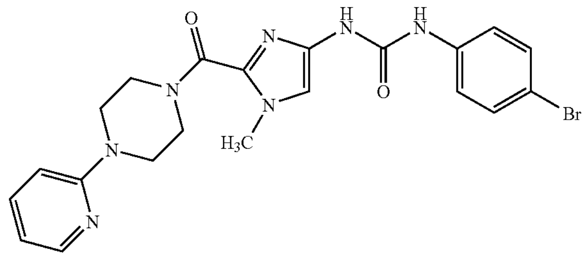 | 484.36 | 484 | 3.899 | Example 23A | 51 (66) |
| 60 | 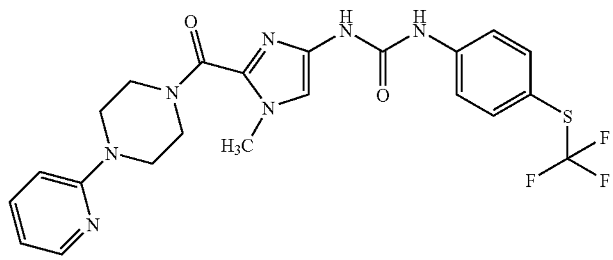 | 505.52 | 506 | 4.260 | Example 23A | 57 (70) |

B. Assessment of the Physiological Activity

The in vitro activity of the compounds of the invention can be shown in the following assays:

Anti-HCMV (Anti-Human Cytomegalovirus) Cytopathogenicity Tests

The test compounds are employed as 50 millimolar (mM) solutions in dimethyl sulfoxide (DMSO). Ganciclovir, foscarnet and cidofovir are used as reference compounds. After the addition of in each case 2 µl of the 50, 5, 0.5 and 0.05 mM DMSO stock solutions to 98 µl portions of cell culture medium in row 2 A-H for duplicate determinations, 1:2 dilutions are carried out with 50 µl portions of medium up to row 11 of the 96-well plate. The wells in rows 1 and 12 each contain 50 µl of medium. Then 150 µl of a suspension of 1×10$^4$ cells (human prepuce fibroblasts [NHDF]) are pipetted into each of the wells (row 1=cell control) and, in rows 2-12, a mixture of HCMV-infected and uninfected NHDF cells (M.O.I.=0.001-0.002), i.e. 1-2 infected cells per 1000 uninfected cells. Row 12 (without substance) serves as virus control. The final test concentrations are 250-0.0005 µM. The plates are incubated at 37° C./5% CO$_2$ for 6 days, i.e. until all the cells in the virus controls are infected (100% cytopathogenic effect [CPE]). The wells are then fixed and stained by adding a mixture of formalin and Giemsa's dye (30 minutes), washed with double-distilled water and dried in a drying oven at 50° C. The plates are then assessed visually using an overhead microscope (Plaque Multiplier from Technomara).

The following data can be acquired from the test plates:

CC$_{50}$ (NHDF)=maximum substance concentration in µM at which no visible cytostatic effects on the cells are evident by comparison with the untreated cell control;

EC$_{50}$ (HCMV)=substance concentration in µM which inhibits the CPE (cytopathic effect) by 50% compared with the untreated virus control;

SI (selectivity index)=CC$_{50}$ (NHDF)/EC$_{50}$ (HCMV).

Representative in vitro activity data of the compounds of the invention are shown in Table A:

TABLE A

| Example No. | NHDF CC$_{50}$ [nM] | HCMV EC$_{50}$ [nM] | SI HCMV |
|---|---|---|---|
| 1 | 43.5 | 3.0 | 14500 |
| 2 | 10.9 | 0.75 | 14530 |
| 25 | 12.5 | 4.8 | 2600 |
| 29 | 34.0 | 0.95 | 35790 |
| 32 | 5.3 | 0.85 | 6240 |

The suitability of the compounds of the invention for the treatment of HCMV infections can be shown in the following animal model:

HCMV Xenograft Gelfoam® Model

Animals:

3-4-week old female immunodeficient mice (16-18 g), Fox Chase SCID or Fox Chase SCID-NOD or SCID beige, are purchased from commercial breeders (Bomholtgaard, Jackson). The animals are kept under sterile conditions (including bedding and feed) in isolators.

Virus Growing:

Human cytomegalovirus (HCMV), Davis strain, is grown in vitro on human embryonic prepuce fibroblasts (NHDF cells). After the NHDF cells have been infected with a multiplicity of infection (M.O.I.) of 0.01, the virus-infected cells are harvested 5-7 days later and stored in the presence of minimal essential medium (MEM), 10% foetal calf serum (FCS) with 10% DMSO at −40° C. After serial ten-fold dilutions of the virus-infected cells, the titre is determined on 24-well plates of confluent NHDF cells after vital staining with Neutral Red, or fixing and staining with a formalin/Giemsa mixture (as described above).

Preparation of the Sponges, Transplantation, Treatment and Evaluation:

Collagen sponges 1×1×1 cm in size (Gelfoam®; Peasel & Lorey, order No. 407534; K. T. Chong et al., Abstracts of 39th Interscience Conference on Antimicrobial Agents and Chemotherapy, 1999, p. 439; P. M. Kraemer et al., Cancer Research 1983, (43): 4822-4827) are initially wetted with phosphate-buffered saline (PBS), the trapped air bubbles are removed by degassing, and then stored in MEM+10% FCS. $1 \times 10^6$ virus-infected NHDF cells (infection with HCMV Davis M.O.I.=0.01) are detached 3 hours after the infection and added dropwise in 20 μl of MEM, 10% of FCS, onto a moist sponge. After 12-13 hours 5 ng/μl basic fibroblast growth factor (bFGF) in 25 μl of PBS/0.1% BSA/1 mM DTT are optionally added to the sponges and the sponges are incubated for 1 hour. For the transplantation, the immunodeficient mice are anaesthetized with avertin or a mixture of azepromazine-xylazine and ketamine, the fur on the back is removed using a dry shaver, the epidermis is opened 1-2 cm, unstressed and the moist sponges are transplanted under the dorsal skin. The surgical wound is closed with tissue glue. 24 hours after the transplantation, the mice are treated with substance perorally three times a day (7.00 h and 14.00 h and 19.00 h), two times a day (8.00 h and 17.00 h) or once a day (14.00 h) over a period of 8 days. The dose is 3 or 10 or 30 or 100 mg/kg of body weight, the volume administered is 10 ml/kg of body weight. The substances are formulated in the form of a 0.5% Tylose suspension, optionally containing 2% DMSO. 9 days after the transplantation and 16 hours after the last administration of substance, the animals are painlessly sacrificed and the sponge is removed. The virus-infected cells are released from the sponge by collagenase digestion (330 U/1.5 ml) and stored in the presence of MEM, 10% foetal calf serum, 10% DMSO at −140° C. Evaluation takes place after serial ten-fold dilutions of the virus-infected cells by determining the titre on 24-well plates of confluent NHDF cells after vital staining with Neutral Red or after fixing and staining with a formalin/Giemsa mixture (as described above). The number of infectious virus particles after the substance treatment compared with the placebo-treated control group is determined.

C. Exemplary Embodiments of Pharmaceutical Compositions

The compounds of the invention can be converted into pharmaceutical preparations in the following ways:

Tablet:
Composition:
100 mg of the compound of Example 1, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of active compound, lactose and starch is granulated with a 5% solution (m/m) of the PVP in water. After drying the granules are mixed with the magnesium stearate for 5 min. This mixture is compressed using a conventional tablet press (see above for format of the tablet). A guideline for the compressive force used for the compression is 15 kN.

Suspension which can be Administered Orally:
Composition:

1000 mg of the compound of Example 1, 1000 mg of ethanol (96%), 400 mg of Rhodigel (xanthan gum from FMC, Pennsylvania, USA) and 99 g of water.

10 ml of oral suspension are equivalent to a single dose of 100 mg of the compound of the invention.

Production:

The Rhodigel is suspended in ethanol, and the active compound is added to the suspension. The water is added while stirring. The mixture is stirred for about 6 h until the swelling of the Rhodigel is complete.

Solution which can be Administered Intravenously:
Composition:

1 mg of the compound of Example 1, 15 g of polyethylene glycol 400 and 250 g of water for injection purposes.

Production:

The compound of the invention is dissolved together with polyethylene glycol 400 in the water with stirring. The solution is sterilized by filtration (pore diameter 0.22 μm) and dispensed under aseptic conditions into heat-sterilized infusion bottles. The latter are closed with infusion stoppers and crimped caps.

The invention claimed is:
1. A compound of formula

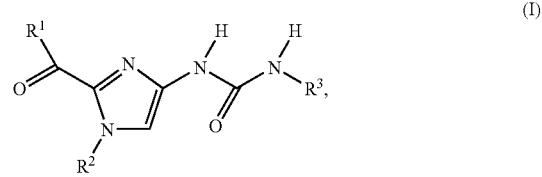

(I)

in which
$R^1$ represents a group of formula

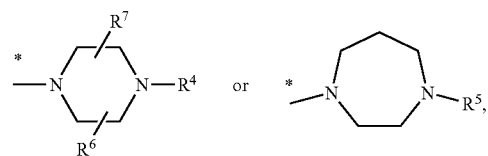

whereby
* represents the linkage site to the carbonyl group,
$R^4$ represents phenyl or 5- or 6-membered heteroaryl,
wherein phenyl and heteroaryl may be substituted with 1 to 3 substituents, whereby the substituents are selected independently of one another from the group consisting of halogen, hydroxy, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, $R^5$ represents phenyl or 5- or 6-membered heteroaryl,
wherein phenyl and heteroaryl may be substituted with 1 to 3 substituents, whereby the substituents are selected independently of one another from the group consisting of halogen, hydroxy, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, and $R^6$ and $R^7$ independently of one another represent hydrogen, methyl or ethyl, $R^2$ represents $C_1$-$C_6$-alkyl,
whereby alkyl may be substituted with a substituent, whereby the substituent is selected from the group consisting of $C_3$-$C_6$-cycloalkyl, $C_6$-$C_{10}$-aryl and 5- or 6-membered heteroaryl,
wherein cycloalkyl, aryl and heteroaryl may be substituted with 1 to 3 substituents, whereby the substituents are selected independently of one another from the group consisting of halogen, hydroxy, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, $R^3$ represents phenyl,
whereby phenyl may be substituted with 1 to 3 substituents, whereby the substituents are selected independently of one another from the group consisting of halogen, hydroxy, trifluoromethyl, difluoromethyl, trifluoromethoxy, difluoromethoxy, monofluoromethoxy, trifluoromethylthio, $C_1$-$C_6$-alkyl and $C_1$-$C_6$-alkoxy, or one of its salts.

2. The compound of claim 1, wherein
$R^1$ represents a group of formula

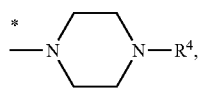

whereby
* represents the linkage site to the carbonyl group,
$R^4$ represents phenyl or 5- or 6-membered heteroaryl,
wherein phenyl and heteroaryl may be substituted with 1 to 3 substituents,
whereby the substituents are selected independently of one another from the group consisting of halogen,
hydroxy, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, $R^2$ represents $C_1$-$C_6$-alkyl,
whereby alkyl may be substituted with a substituent, whereby the substituent is selected from the group consisting of $C_3$-$C_6$-cycloalkyl and phenyl,
wherein cycloalkyl and phenyl may be substituted with 1 to 3 substituents, whereby the substituents are selected independently of one another from the group consisting of halogen, hydroxy, oxo, nitro, cyano, trifluoromethyl, difluoromethyl, trifluoromethoxy, difluoromethoxy, monofluoromethoxy, trifluoromethylthio, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, $R^3$ represents phenyl,
whereby phenyl may be substituted with 1 to 3 substituents, whereby the substituents are selected independently of one another from the group consisting of halogen, hydroxy, trifluoromethyl, difluoromethyl, trifluoromethoxy, difluoromethoxy, monofluoromethoxy, trifluoromethylthio, $C_1$-$C_6$-alkyl and $C_1$-$C_6$-alkoxy.

3. The compound of claim 1, wherein
$R^1$ represents a group of formula

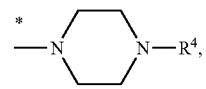

whereby
* represents the linkage site to the carbonyl group,
$R^4$ represents phenyl or pyridyl,
wherein phenyl and pyridyl may be substituted with 1 to 3 substituents, whereby the substituents are selected independently of one another from the group consisting of halogen, nitro, cyano, trifluoromethyl, difluoromethyl, trifluoromethoxy, difluoromethoxy, monofluoromethoxy, $C_1$-$C_4$-alkyl and $C_1$-$C_4$-alkoxy, $R^2$ represents methyl, ethyl or n-butyl,
whereby methyl, ethyl and n-butyl may be substituted with a substituent, whereby the substituent is selected from the group consisting of cyclopropyl and phenyl,
wherein phenyl may be substituted with a trifluoromethyl substituent, $R^3$ represents phenyl,
whereby phenyl may be substituted with 1 to 3 substituents, whereby the substituents are selected independently of one another from the group consisting of fluorine, chlorine, trifluoromethoxy, difluoromethoxy, trifluoromethylthio and methyl.

4. A method for preparing a compound of formula (I) of claim 1, wherein according to method [A] a compound of formula

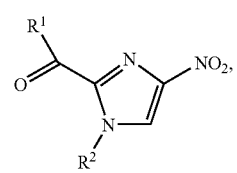

(II)

in which
$R^1$ and $R^2$ have the meaning indicated in claim 1, is reacted in the first step with a reducing agent and in the second step in the presence of a carbonic acid derivative selected from the group consisting of N,N-carbonyldiimidazole, phosgene, diphosgene, triphosgene, phenyl chloroformate, and 4-nitrophenyl chloroformate with a compound of formula $$H_2N—R^3 \qquad (III),$$

in which
$R^3$ has the meaning indicated in claim 1,
or
according to method [B] a compound of formula (II) is reacted in the first step with a reducing agent and in the second step with a compound of formula $$OCN—R^3 \qquad (IV),$$

in which
$R^3$ has the meaning indicated in claim 1,
or
according to method [C] a compound of formula

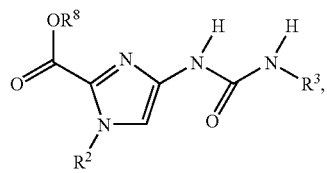

(V)

in which
$R^2$ and $R^3$ have the meaning indicated in claim 1, and
$R^8$ represents methyl or ethyl,
is reacted in the first step with a base and in the second step with a compound of formula $$R^1—H \qquad (VI),$$

in which
$R^1$ has the meaning indicated in claim 1,
in the presence of dehydrating reagents.

5. A medicament, comprising a compound of claim 1 in combination with at least one inert nontoxic, pharmaceutically acceptable excipient.

6. A method for the production of a medicament for the treatment of viral infections using a compound of claim 1.

7. A method for controlling viral infections in humans and animals by administering an antivirally effective amount of at least one compound of claim 1, wherein the viral infection is an infection with the human cytomegalovirus (HCMV) or another representative of the group of *Herpes viridae*.

8. A method for controlling viral infections in humans and animals by administering an antivirally effective amount of at least one medicament of claim 5, wherein the viral infection is an infection with the human cytomegalovirus (HCMV) or another representative of the group of *Herpes viridae*.

9. A method for controlling viral infections in humans and animals by administering an antivirally effective amount of at least one medicament obtained in the method of claim 6, wherein the viral infection is an infection with the human cytomegalovirus (HCMV) or another representative of the group of *Herpes viridae*.

* * * * *

UNITED STATES PATENT AND TRADEMARK OFFICE
CERTIFICATE OF CORRECTION

PATENT NO. : 7,919,489 B2
APPLICATION NO. : 11/894307
DATED : April 5, 2011
INVENTOR(S) : Holger Zimmermann et al.

Page 1 of 1

It is certified that error appears in the above-identified patent and that said Letters Patent is hereby corrected as shown below:

Column 60
Lines 43-45, please replace "$EC_{50}$ (HCMV)=substance concentration in μM which inhibits the CPE (cytopathic effect) by 50% compared with the untreated virus control" with -- $EC_{50}$ (HCMV)=substance concentration in nM which inhibits the CPE (cytopathic effect) by 50% compared with the untreated virus control--

Line 53 in the second column of Table A, please replace "$CC_{50}$ [nM]" with --$CC_{50}$ [μM]--

Signed and Sealed this
Thirtieth Day of October, 2012

David J. Kappos
*Director of the United States Patent and Trademark Office*